(12) United States Patent
Wexler et al.

(10) Patent No.: US 8,937,650 B2
(45) Date of Patent: Jan. 20, 2015

(54) SYSTEMS AND METHODS FOR PERFORMING A TRIGGERED ACTION

(71) Applicants: Yonatan Wexler, Jerusalem (IL); Amnon Shashua, Zion (IL)

(72) Inventors: Yonatan Wexler, Jerusalem (IL); Amnon Shashua, Zion (IL)

(73) Assignee: OrCam Technologies Ltd., Jerusalem (IL)

( * ) Notice: Subject to any disclaimer, the term of this patent is extended or adjusted under 35 U.S.C. 154(b) by 0 days.

(21) Appl. No.: 14/135,762

(22) Filed: Dec. 20, 2013

(65) Prior Publication Data

US 2014/0267644 A1    Sep. 18, 2014

Related U.S. Application Data

(60) Provisional application No. 61/799,649, filed on Mar. 15, 2013, provisional application No. 61/830,122, filed on Jun. 2, 2013.

(51) Int. Cl.
*H04N 7/18* (2006.01)
*A61F 9/08* (2006.01)
*G06K 9/00* (2006.01)

(52) U.S. Cl.
CPC .............. *A61F 9/08* (2013.01); *G06K 9/00671* (2013.01)
USPC .......................................................... 348/62

(58) Field of Classification Search
USPC .......................................................... 348/62
See application file for complete search history.

(56) References Cited

U.S. PATENT DOCUMENTS

| 6,115,482 | A | 9/2000 | Sears et al. |
| 7,876,317 | B2* | 1/2011 | Zhang et al. .................. 345/419 |
| 2004/0168131 | A1* | 8/2004 | Blumberg ...................... 715/534 |
| 2005/0208457 | A1 | 9/2005 | Fink et al. |
| 2006/0017810 | A1 | 1/2006 | Kurzweil et al. |
| 2010/0005009 | A1* | 1/2010 | Lin-Hendel ..................... 705/27 |
| 2012/0212593 | A1 | 8/2012 | Na'aman et al. |
| 2012/0236180 | A1* | 9/2012 | Lin ............................... 348/239 |

(Continued)

FOREIGN PATENT DOCUMENTS

EP    2065871    6/2009

OTHER PUBLICATIONS

U.S. Appl. No. 14/136,438, filed Dec. 20, 2013, entitled "Apparatus, Method, and Computer Readable Medium for Expedited Text Reading Using Staged OCR Technique."

(Continued)

*Primary Examiner* — Dave Czekaj
*Assistant Examiner* — Tracy Li
(74) *Attorney, Agent, or Firm* — Finnegan, Henderson, Farabow, Garrett & Dunner, LLP

(57) ABSTRACT

A device and method are provided for performing a triggered action. In one implementation, an apparatus for processing real time images of an environment of a user is provided. The apparatus may include an image sensor configured to capture image data for providing a plurality of sequential images of the environment of the user. The apparatus may also include at least one processor device configured to identify a trigger associated with a desire of the user to cause at least one pre-defined action associated with an object. The trigger may include an erratic movement of the object. In response to identification of the trigger, the at least one processor device may also be configured to identify a captured representation of the object. Based on at least the captured representation of the object, the at least one processor device may be configured to execute the at least one pre-defined action.

28 Claims, 26 Drawing Sheets

(56) References Cited

U.S. PATENT DOCUMENTS

| | | | |
|---|---|---|---|
| 2013/0041950 A1* | 2/2013 | Chan | 709/204 |
| 2013/0073583 A1* | 3/2013 | Licata et al. | 707/769 |
| 2013/0169536 A1 | 7/2013 | Wexler et al. | |
| 2013/0182905 A1* | 7/2013 | Myers et al. | 382/103 |
| 2013/0266205 A1* | 10/2013 | Valpola | 382/153 |
| 2013/0271584 A1 | 10/2013 | Wexler et al. | |

OTHER PUBLICATIONS

U.S. Appl. No. 14/135,727, filed Dec. 20, 2013, entitled "Systems and Method for Audible Facial Recognition."

U.S. Appl. No. 14/137,033, filed Dec. 20, 2013, entitled "Apparatus and Method for Providing Failed-Attempt Feedback Using a Camera on Glasses."

U.S. Appl. No. 14/137,263, filed Dec. 20, 2013, entitled "Apparatus and Method for Executing System Commands Based on Captured Image Data."

U.S. Appl. No. 14/135,757, filed Dec. 20, 2013, entitled "Systems and Methods for Automatic Control of a Continuous Action."

U.S. Appl. No. 14/137,373, filed Dec. 20, 2013, entitled "Apparatus and Method for Automatic Action Selection Based on Image Context."

U.S. Appl. No. 14/137,328, filed Dec. 20, 2013, entitled "Apparatus and Method for Performing Actions Based on Captured Image Data."

U.S. Appl. No. 14/135,859, filed Dec. 20, 2013, entitled "Apparatus Connectable to Glasses."

U.S. Appl. No. 14/137,446, filed Dec. 20, 2013, entitled "Apparatus and Method for Hierarchical Object Identification Using a Camera on Glasses."

U.S. Appl. No. 14/135,928, filed Dec. 20, 2013, entitled "Systems and Methods for Processing Images."

U.S. Appl. No. 14/135,775, filed Dec. 20, 2013, entitled "Systems and Methods for Providing Feedback Based on the State of an Object."

U.S. Appl. No. 14/137,522, filed Dec. 20, 2013, entitled "Apparatus and Method for Using Background Change to Determine Context."

U.S. Appl. No. 14/136,545, filed Dec. 20, 2013, entitled "Apparatus, Method, and Computer Readable Medium for Recognizing Text on a Curved Survace."

U.S. Appl. No. 14/137,384, filed Dec. 20, 2013, entitled "Systems and Methods for Audibly Presenting Textual Information Included in Image Data."

U.S. Appl. No. 14/136,876, filed Dec. 20, 2013, entitled "Apparatus and Method for Analyzing Images."

Karacs, Kristof et al., "Bionic Eyeglass: An Audio Guide for Visually Impaired," Biomedical Circuits and Systems Conference, 2006, BIOCAS 2006, IEEE, Piscataway, NJ, Nov. 29, 2006, p. 190-193.

Lai, Chin-Lun et al., "An Integrated Portable Vision Assistant Agency for the Visual Impaired People," 2009 IEEE International Conference on Control and Automation, Christchurch, New Zealand, Dec. 9-11, 2009 (6 pages).

* cited by examiner

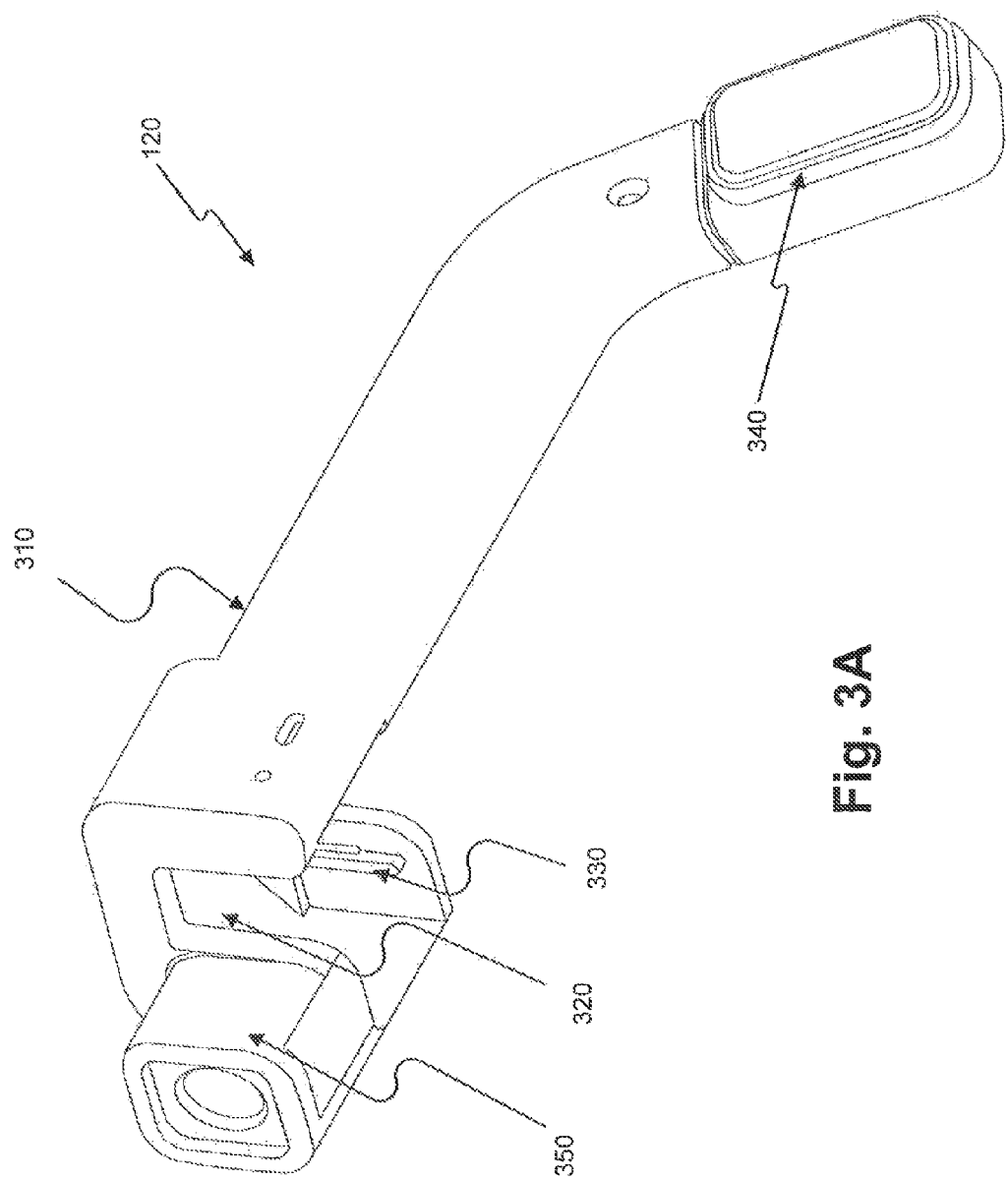

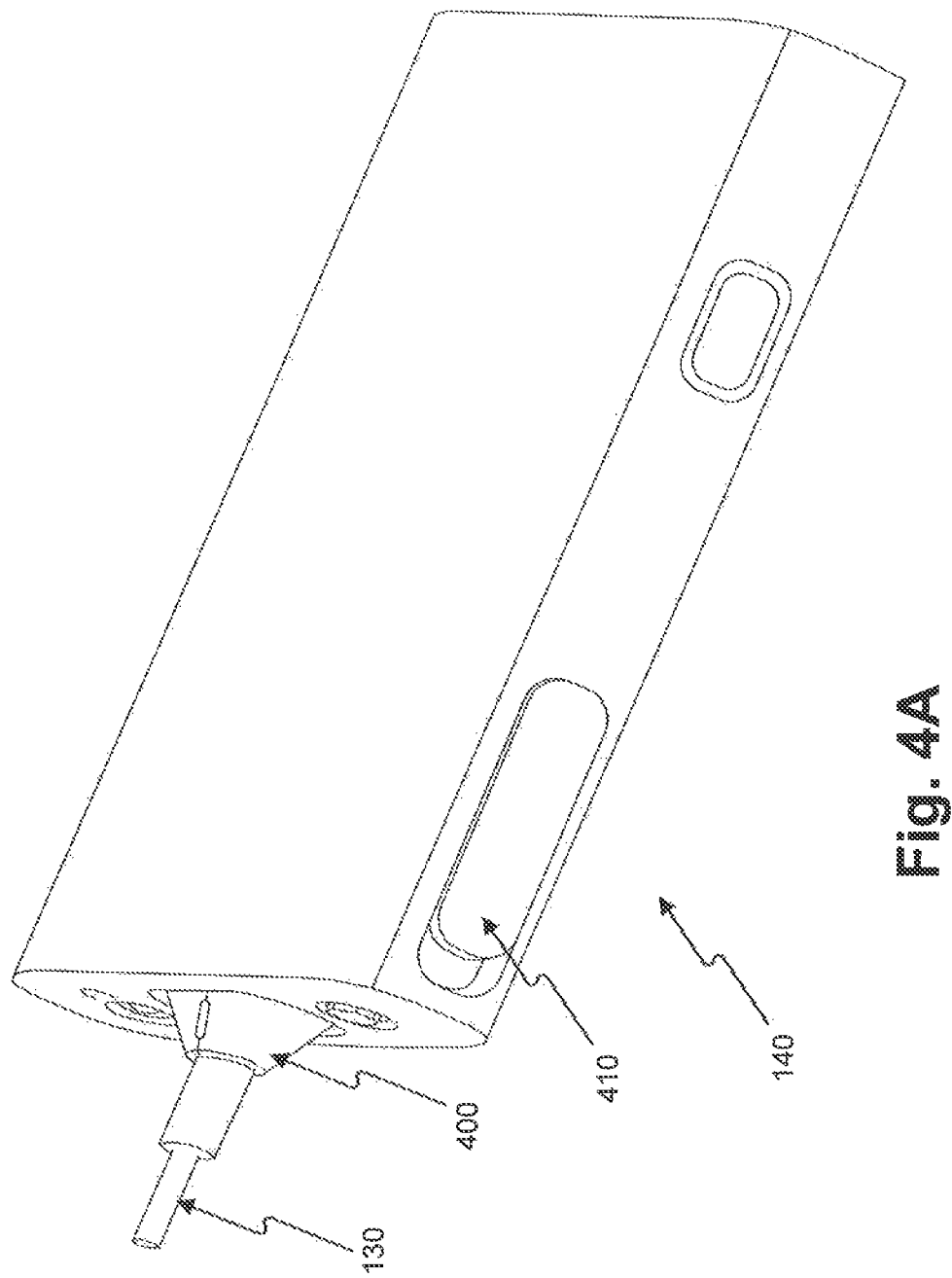

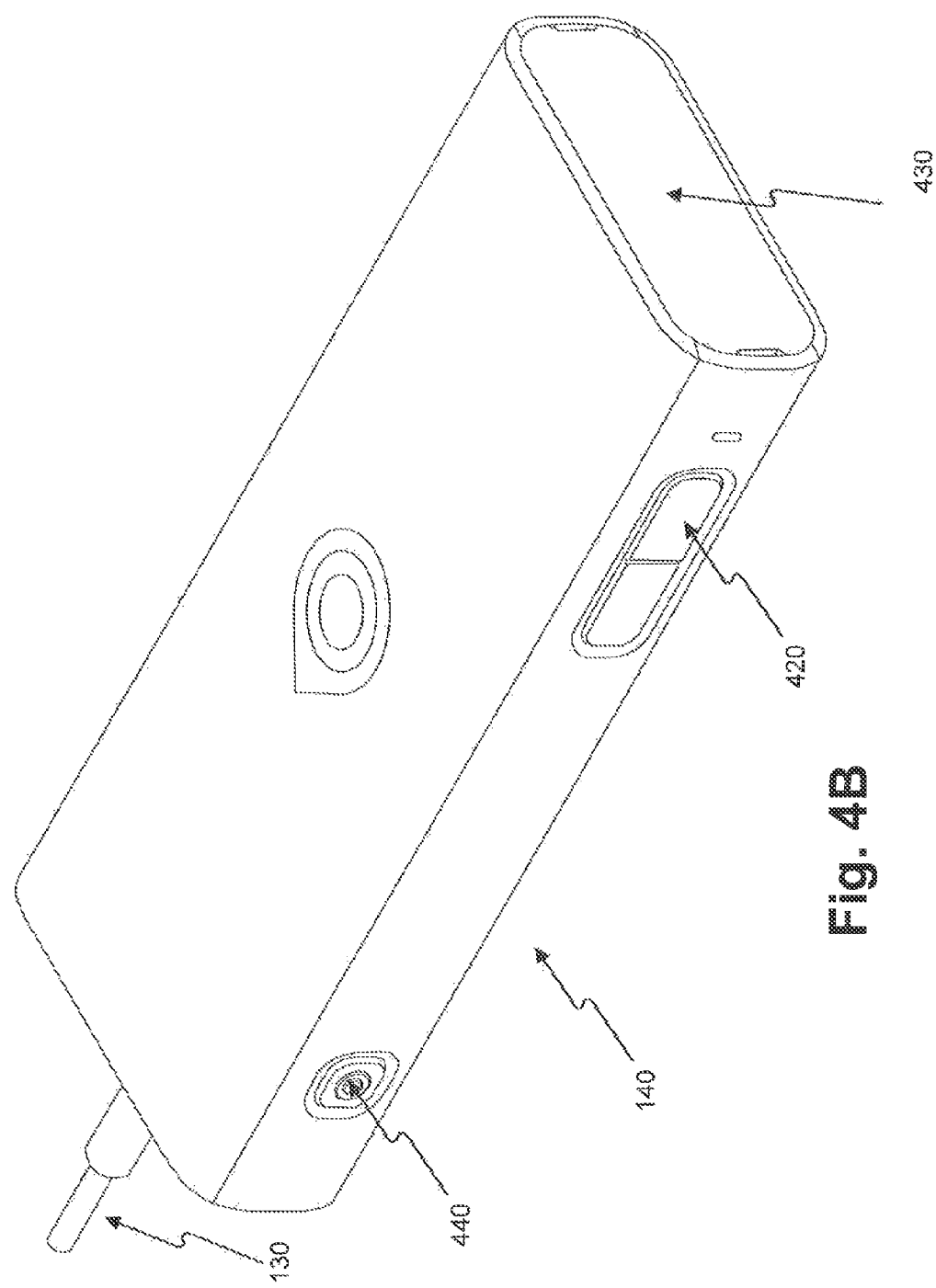

US 8,937,650 B2

SYSTEMS AND METHODS FOR PERFORMING A TRIGGERED ACTION

CROSS REFERENCE TO RELATED APPLICATIONS

This application claims the benefit of priority of U.S. Provisional Patent Application No. 61/799,649, filed on Mar. 15, 2013, and U.S. Provisional Patent Application No. 61/830, 122, filed on Jun. 2, 2013, both of which are incorporated herein by reference in their entirety.

BACKGROUND

I. Technical Field

This disclosure generally relates to devices and methods for providing information to a user. More particularly, this disclosure relates to devices and methods for providing information to a user by processing images captured from the environment of the user.

II. Background Information

Visual acuity is an indication of the clarity or clearness of a person's vision that is commonly measured twenty feet from an object. When measuring visual acuity, the ability of a person to identify black symbols on a white background at twenty feet is compared to the ability of a person with normal eyesight. This comparison can be symbolized by a ratio. For example, a ratio of 20/70 vision means a person located at a distance of twenty feet can see what a person with normal vision can see at seventy feet. A person has low vision if he or she has a visual acuity between 20/70 and 20/200 in the better-seeing eye that cannot be corrected or improved with regular eyeglasses. The prevalence of low vision is about one in a hundred for people in their sixties and rapidly increases to one in five for people in their nineties. Low vision may also depend on the environment. For example, some individuals may be able to see only when there is ample light.

A person may have low vision (also known as visual impairment) for several reasons. Other than eye damage and failure of the brain to receive visual cues sent by the eyes, different medical conditions may cause visual impairment. Medical conditions that may cause visual impairment include Age-related Macular Degeneration (AMD), retinitis pigmentosa, cataract, and diabetic retinopathy.

AMD, which usually affects adults, is caused by damage to the retina that diminishes vision in the center of a person's visual field. The lifetime risk for developing AMD is strongly associated with certain genes. For example, the lifetime risk of developing AMD is 50% for people that have a relative with AMD, versus 12% for people that do not have relatives with AMD.

Retinitis pigmentosa is an inherited, degenerative eye disease that causes severe vision impairment and often blindness. The disease process begins with changes in pigment and damage to the small arteries and blood vessels that supply blood to the retina. There is no cure for retinitis pigmentosa and no known treatment can stop the progressive vision loss caused by the disease.

A cataract is a clouding of the lens inside the eye which leads to a decrease in vision. Over time, a yellow-brown pigment is deposited within the lens and obstructs light from passing and being focused onto the retina at the back of the eye. Biological aging is the most common cause of a cataract, but a wide variety of other risk factors (e.g., excessive tanning, diabetes, prolonged steroid use) can cause a cataract.

Diabetic retinopathy is a systemic disease that affects up to 80% of all patients who have had diabetes for ten years or more. Diabetic retinopathy causes microvascular damage to a blood-retinal barrier in the eye and makes the retinal blood vessels more permeable to fluids.

People with low vision experience difficulties due to lack of visual acuity, field-of-view, color perception, and other visual impairments. These difficulties affect many aspects of everyday life. Persons with low vision may use magnifying glasses to compensate for some aspects of low vision. For example, if the smallest letter a person with 20/100 vision can read is five times larger than the smallest letter that a person with 20/20 vision can read, then 5× magnification should make everything that is resolvable to the person with 20/20 vision resolvable to the person with low vision. However, magnifying glasses are expensive and cannot remedy all aspects of low vision. For example, a person with low vision who wears magnifying glasses may still have a difficult time recognizing details from a distance (e.g., people, signboards, traffic lights, etc.). Accordingly, there is a need for other technologies that can assist people who have low vision accomplish everyday activities.

SUMMARY

Embodiments consistent with the present disclosure provide devices and methods for providing information to a user by processing images captured from the environment of the user. The disclosed embodiments may assist persons who have low vision.

In accordance with a disclosed embodiment, an apparatus for processing real time images of an environment of a user is disclosed. The apparatus may include an image sensor configured to capture image data for providing a plurality of sequential images of the environment of the user. The apparatus may also include at least one processor device configured to identify, using the image data, a trigger associated with a desire of the user to cause at least one pre-defined action associated with an object. The trigger may include an erratic movement of the object. In response to identification of the trigger, the at least one processor device may also be configured to identify in the image data a captured representation of the object. Based on at least the captured representation of the object, the at least one processor device may be configured to execute the at least one pre-defined action.

Consistent with another disclosed embodiment, an apparatus for processing real time images of an environment of a user is disclosed. The apparatus may include an image sensor configured to be worn by the user and to capture image data for providing a plurality of sequential images of the environment of the user. The apparatus may also include at least one processor device configured to identify, using the image data, a trigger associated with a desire of the user to cause at least one pre-defined action associated with an object. The trigger may include a predefined movement sequence of the object. In response to identification of the trigger, the at least one processor device may also be configured to identify in the image data a captured representation of the object. Based on at least the captured representation of the object, the at least one processor device may be configured to execute the at least one pre-defined action.

Consistent with another disclosed embodiment, a method for providing feedback to a user is disclosed. The method may include capturing real time image data from an environment of the user. The method may also include identifying in the image data a trigger associated with a desire of the user to cause at least one pre-defined action associated with an object. The trigger may include an erratic movement of the object. The method may further include, based on identification of the trigger, identifying in the image data a captured representation of the object, and, based on at least the captured representation of the object, executing the at least one pre-defined action.

Consistent with other disclosed embodiments, non-transitory computer-readable storage media may store program instructions, which are executed by at least one processor device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate various disclosed embodiments. In the drawings:

FIG. 3A is a schematic illustration of an example of a sensory unit from a first viewpoint;

FIG. 4A is a schematic illustration of an example of a processing unit from a first viewpoint;

FIG. 4B is a schematic illustration of the processing unit shown in FIG. 4A from a second viewpoint;

DETAILED DESCRIPTION

Figure 1:
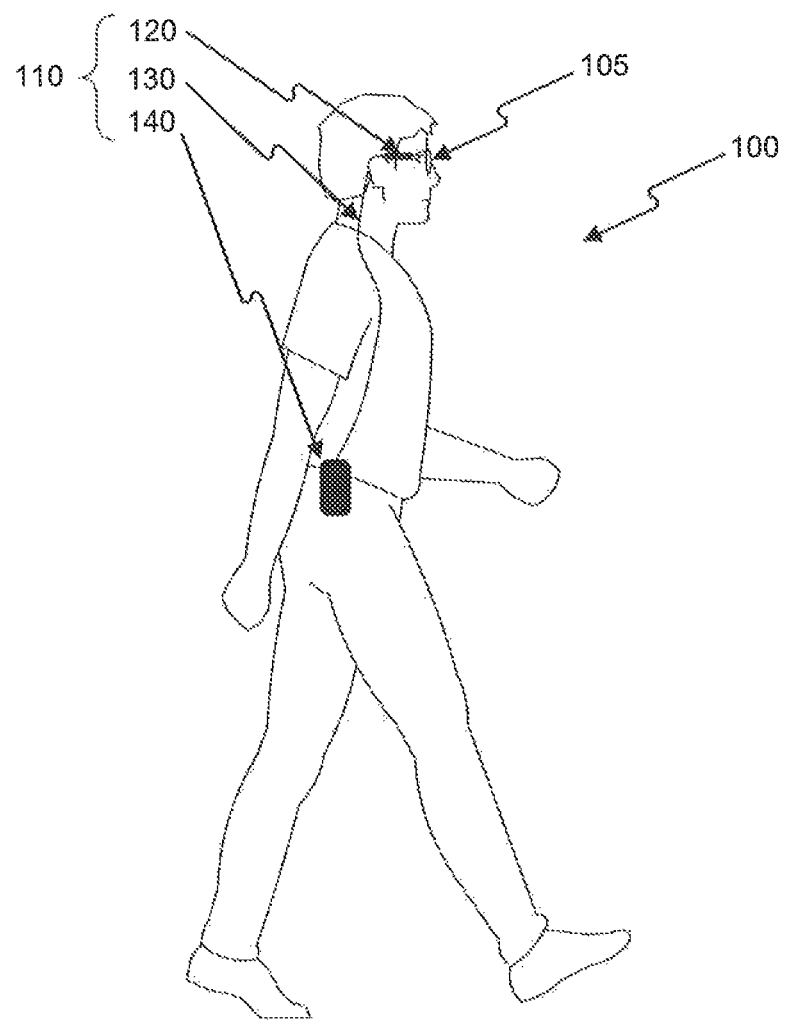
FIG. 1 is a schematic illustration of a user wearing an apparatus for aiding persons who have low vision.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Disclosed embodiments provide devices and methods for assisting people who have low vision. One example of the disclosed embodiments is a device that includes a camera configured to capture real-time image data from the environment of the user. The device also includes a processing unit configured to process the real-time image data and provide real-time feedback to the user. The real-time feedback may include, for example, an output that audibly identifies individuals from a distance, reads signboards, and/or identifies the state of a traffic light.

FIG. 1 illustrates a user 100 wearing an apparatus 110 connected to glasses 105, consistent with a disclosed embodiment. Apparatus 110 may provide functionality for aiding user 100 with various daily activities that are otherwise difficult for user 100 to accomplish due to low vision. Glasses 105 may be prescription glasses, magnifying glasses, non-prescription glasses, safety glasses, sunglasses, etc.

As shown in FIG. 1, apparatus 110 includes a sensory unit 120 and a processing unit 140. Sensory unit 120 may be connected to a support (not shown in FIG. 1) that is mounted on glasses 105. In addition, sensory unit 120 may include an image sensor (not shown in FIG. 1) for capturing real-time image data of the field-of-view of user 100. The term "image data" includes any form of data retrieved from optical signals in the near-infrared, infrared, visible, and ultraviolet spectrums. The image data may be used to form video clips and/or photographs.

Processing unit 140 may communicate wirelessly or via a wire 130 connected to sensory unit 120. In some embodiments, processing unit 140 may produce an output of audible feedback to user 100 (e.g., using a speaker or a bone conduction headphone).

Apparatus 110 is one example of a device capable of implementing the functionality of the disclosed embodiments. Other devices capable of implementing the disclosed embodiments include, for example, a mobile computer with a camera (e.g., a smartphone, a smartwatch, a tablet, etc.) or a clip-on-camera configured to communicate with a processing unit (e.g., a smartphone or a dedicated processing unit, which can be carried in a pocket). A person skilled in the art will appreciate that different types of devices and arrangements of devices may implement the functionality of the disclosed embodiments.

Figure 2A:
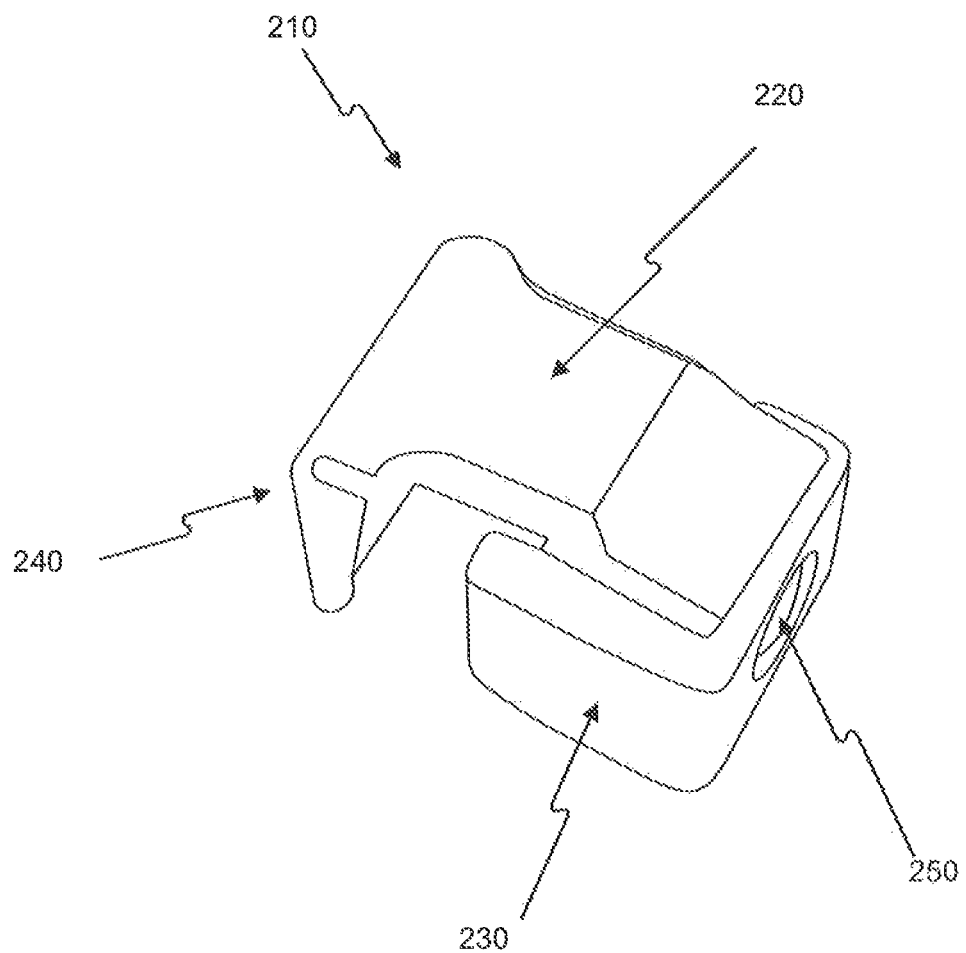
FIG. 2A is a schematic illustration of an example of a support from a first viewpoint.

FIG. 2A is a schematic illustration of an example of a support 210. As discussed in connection with FIG. 1, support 210 may be mounted on glasses 105 and connect to sensory unit 120. The term "support" includes any device or structure that enables detaching and reattaching of a device including a camera to a pair of glasses or to another object (e.g., a helmet). Support 210 may be made from plastic (e.g., polycarbonate), metal (e.g., aluminum), or a combination of plastic and metal (e.g., carbon fiber graphite). Support 210 may be mounted on glasses 105 using screws, bolts, snaps, or any fastening means used in the art.

As shown in FIG. 2A, support 210 includes a base 230 connected to a clamp 240. A bridge 220 connects base 230 with clamp 240. Base 230 and clamp 240 enable sensory unit 120 to easily attach to and detach from support 210. In one embodiment, base 230 may include an internally threaded member 250 for cooperating with a screw (not shown in FIG. 2A) to mount support 210 on glasses 105.

Figure 2B:
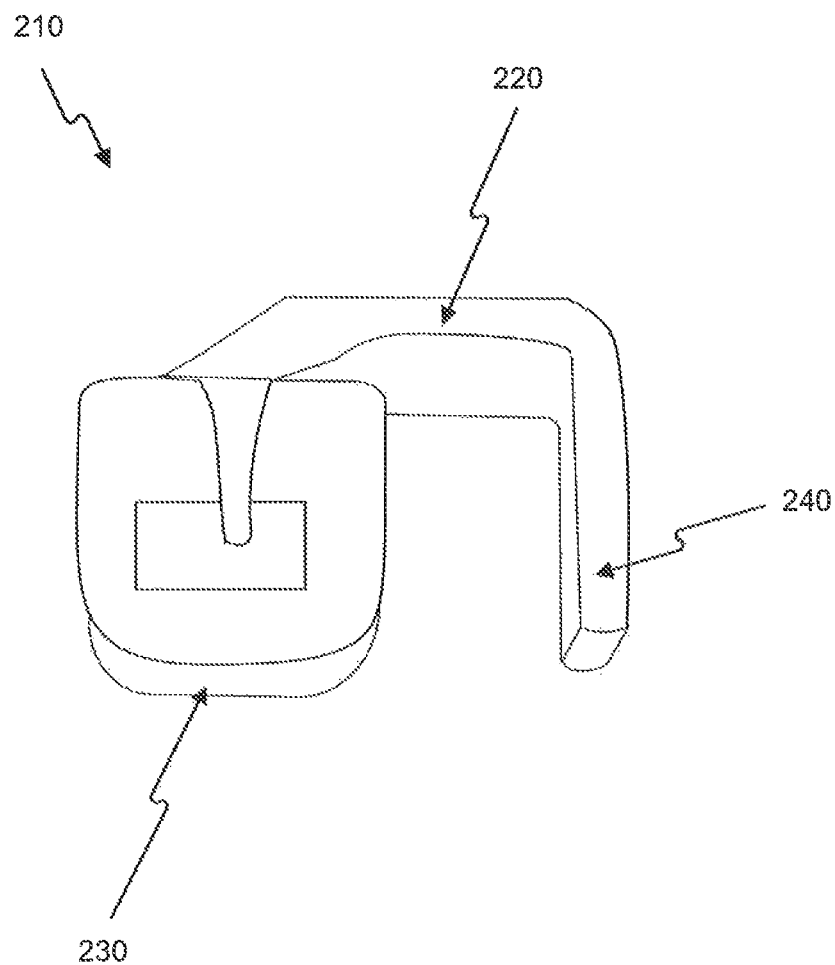
FIG. 2B is a schematic illustration of the support shown in FIG. 2A from a second viewpoint.

FIG. 2B illustrates support 210 from a second viewpoint. The viewpoint shown in FIG. 2B is from a side orientation of support 210.

Figure 2C:
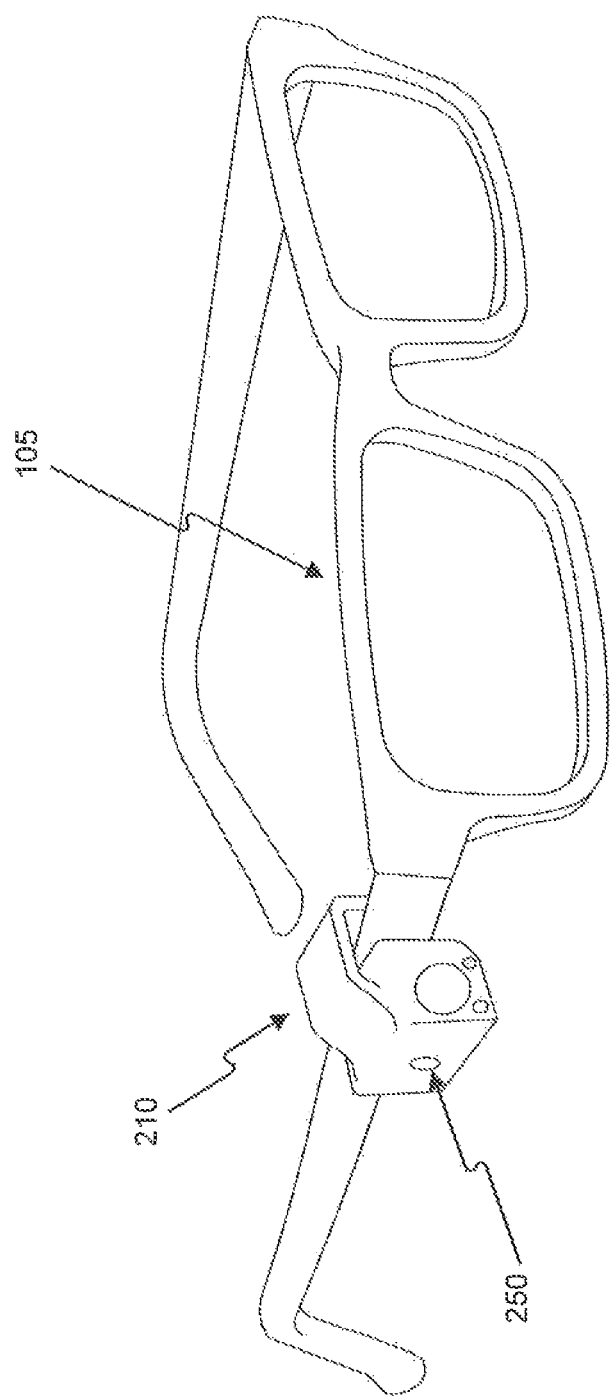
FIG. 2C is a schematic illustration of the support shown in FIG. 2A mounted on a pair of glasses.

FIG. 2C illustrates support 210 mounted on glasses 105. Support 210 may be configured for mounting on any kind of glasses (e.g., eyeglasses, sunglasses, 3D glasses, safety glasses, etc.). As shown in FIG. 2C, sensory unit 120 is not attached to support 210 and, accordingly, support 210 may be sold separately from apparatus 110. This arrangement makes apparatus 110 compatible with a variety of glasses. For example, some users may have several pairs of glasses and may wish to mount a support on each pair of glasses.

In other embodiments, support 210 may be an integral part of a pair of glasses, or sold and installed by an optometrist. For example, support 210 may be configured for mounting on the arms of glasses 105 near the frame front, but before the hinge. Alternatively, support 210 may be configured for mounting on the bridge of glasses 105.

Figure 2D:
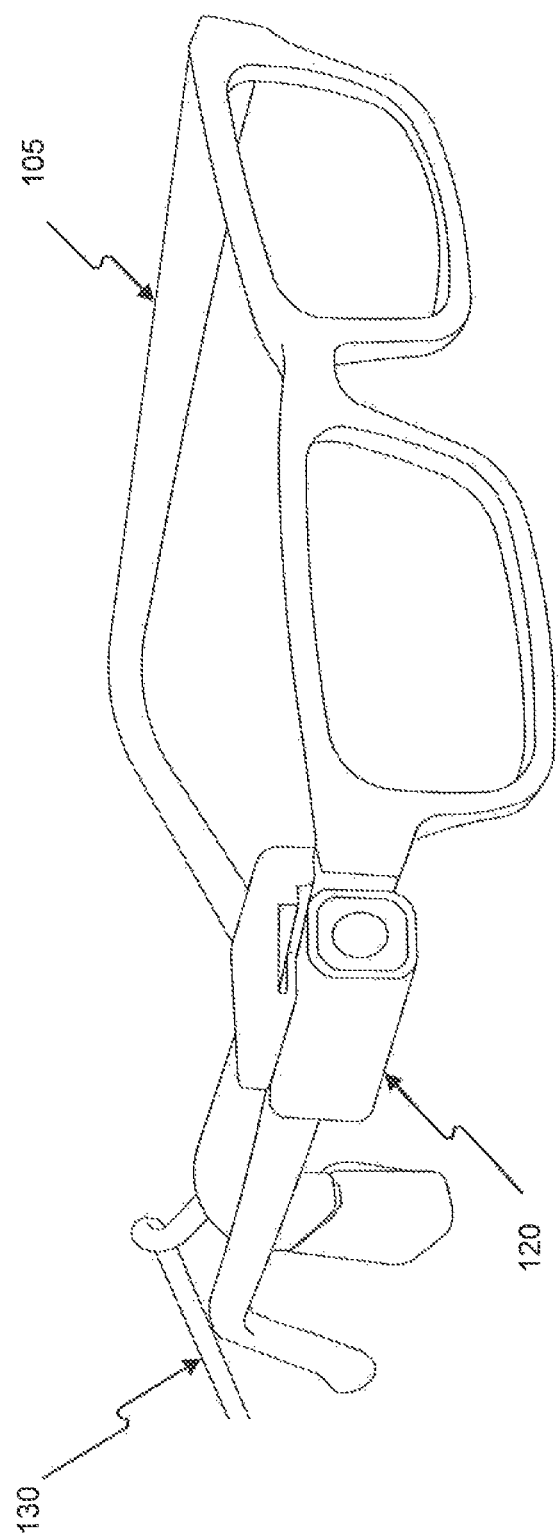
FIG. 2D is a schematic illustration of a sensory unit attached to the support that is mounted on the pair of glasses shown in FIG. 2C.

FIG. 2D illustrates sensory unit 120 attached to support 210 (not visible in FIG. 2D), and support 210 mounted on glasses 105. In some embodiments, support 210 may include a quick release mechanism for disengaging and reengaging sensory unit 120. For example, support 210 and sensory unit 120 may include magnetic elements. As an alternative example, support 210 may include a male latch member and sensory unit 120 may include a female receptacle.

When sensory unit 120 is attached (or reattached) to support 210, the field-of-view of a camera associated with sensory unit 120 may be substantially identical to the field-of-view of user 100. Accordingly, in some embodiments, after support 210 is attached to sensory unit 120, directional calibration of sensory unit 120 may not be required because sensory unit 120 aligns with the field-of-view of user 100.

In other embodiments, support 210 may include an adjustment component (not shown in FIG. 2D) to enable calibration of the aiming direction of sensory unit 120 in a substantially set position that is customized to user 100 wearing glasses 105. For example, the adjustment component may include an adjustable hinge to enable vertical and horizontal alignment of the aiming direction of sensory unit 120. Adjusting the alignment of sensory unit 120 may assist users who have a unique and individual visual impairment. The adjustment may be internal or external to sensory unit 120.

Figure 2E:
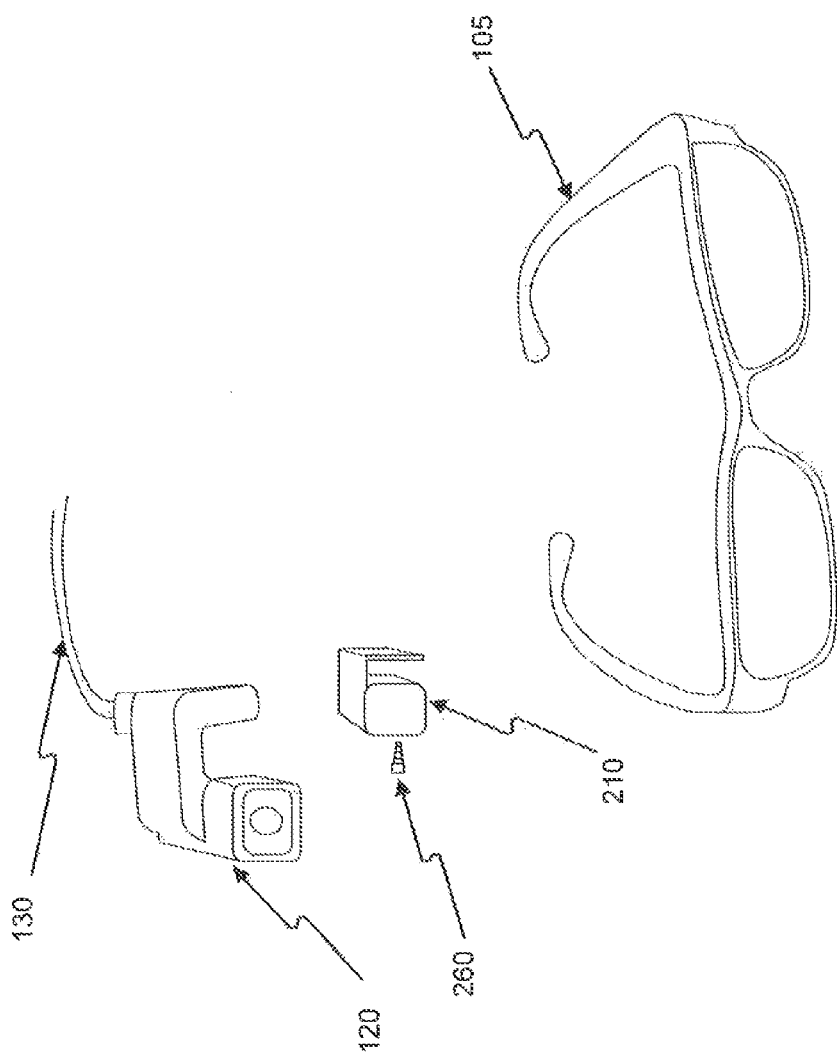
FIG. 2E is an exploded view of FIG. 2D.

FIG. 2E is an exploded view of the components shown in FIG. 2D. Sensory unit 120 may be attached to glasses 105 in the following way. Initially, support 210 may be mounted on glasses 105 using screw 260. Next, screw 260 may be inserted into internally threaded member 250 (not shown in FIG. 2E) in the side of support 210. Sensory unit 120 may then be clipped on support 210 such that it is aligned with the field-of-view of user 100.

FIG. 3A is a schematic illustration of sensory unit 120 from a first viewpoint. As shown in FIG. 3A, sensory unit 120 includes a feedback-outputting unit 340 and an image sensor 350.

Sensory unit 120 is configured to cooperate with support 210 using clip 330 and groove 320, which fits the dimensions of support 210. The term "sensory unit" refers to any electronic device configured to capture real-time images and provide a non-visual output. Furthermore, as discussed above, sensory unit 120 includes feedback-outputting unit 340. The term "feedback-outputting unit" includes any device configured to provide information to a user.

In some embodiments, feedback-outputting unit 340 may be configured to be used by blind persons and persons with low vision. Accordingly, feedback-outputting unit 340 may be configured to output nonvisual feedback. The term "feedback" refers to any output or information provided in response to processing at least one image in an environment. For example, feedback may include a descriptor of a branded product, an audible tone, a tactile response, and/or information previously recorded by user 100. Furthermore, feedback-outputting unit 340 may comprise appropriate components for outputting acoustical and tactile feedback that people with low vision can interpret. For example, feedback-outputting unit 340 may comprise audio headphones, a speaker, a bone conduction headphone, interfaces that provide tactile cues, vibrotactile stimulators, etc.

As discussed above, sensory unit 120 includes image sensor 350. The term "image sensor" refers to a device capable of detecting and converting optical signals in the near-infrared, infrared, visible, and ultraviolet spectrums into electrical signals. The electric signals may be used to form an image based on the detected signal. For example, image sensor 350 may be part of a camera. In some embodiments, when sensory unit 120 is attached to support 210, image sensor 350 may acquire a set aiming direction without the need for directional calibration. The set aiming direction of image sensor 350 may substantially coincide with the field-of-view of user 100 wearing glasses 105. For example, a camera associated with image sensor 350 may be installed within sensory unit 120 in a predetermined angle in a position facing slightly downwards (e.g., 5-15 degrees from the horizon). Accordingly, the set aiming direction of image sensor 350 may match the field-of-view of user 100.

As shown in FIG. 3A, feedback-outputting unit 340 and image sensor 350 are included in a housing 310. The term "housing" refers to any structure that at least partially covers, protects, or encloses a sensory unit. The housing may be made from one or more different materials (e.g., plastic or aluminum). In one embodiment, housing 310 may be designed to engage with a specific pair of glasses having a specific support (e.g., support 210). In an alternative embodiment, housing 310 may be designed to engage more than one pair of glasses, each having a support (e.g., support 210) mounted thereon. Housing 310 may include a connector for receiving power from an external mobile-power-source or an internal mobile-power-source, and for providing an electrical connection to image sensor 350.

Figure 3B:
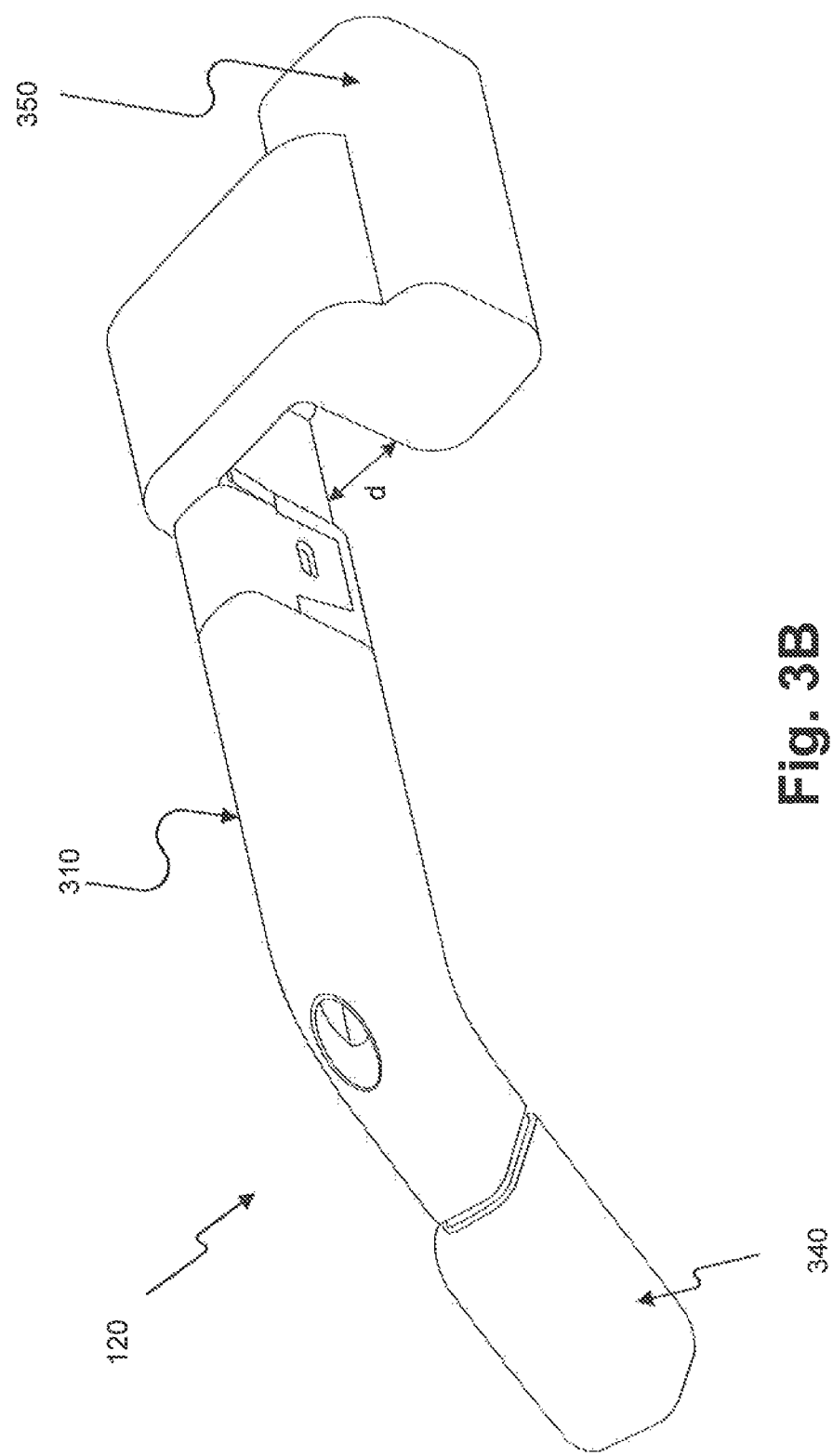
FIG. 3B is a schematic illustration of the sensory unit shown in FIG. 3A from a second viewpoint.

FIG. 3B is a schematic illustration of sensory unit 120 from a second viewpoint. As shown in FIG. 3B, housing 310 includes a U-shaped element. An inner distance "d" between each side of the U-shaped element is larger than the width of the arm of glasses 105. Additionally, the inner distance "d" between each side of the U-shaped element is substantially equal to a width of support 210. The inner distance "d" between each side of the U-shaped element may allow user 100 to easily attach housing 310 to support 210, which may be mounted on glasses 105. As illustrated in FIG. 3B, image sensor 350 is located on one side of the U-shaped element and feedback-outputting unit 340 is located on another side of the U-shaped element.

Figure 3C:
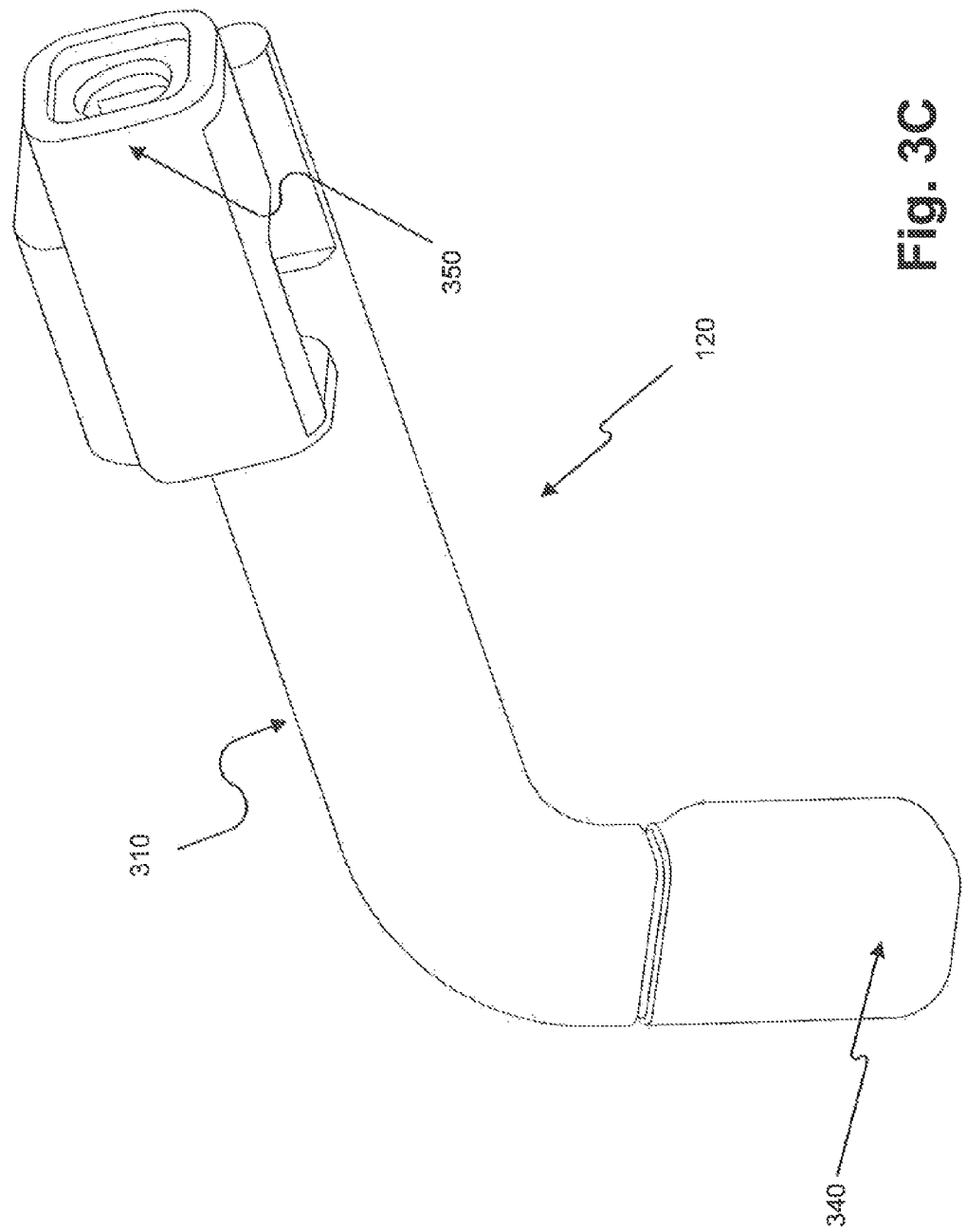
FIG. 3C is a schematic illustration of the sensory unit shown in FIG. 3A from a third viewpoint.

FIG. 3C is a schematic illustration of sensory unit 120 from a third viewpoint. The viewpoint shown in FIG. 3C is from a side orientation of sensory unit 120 and shows the side of the U-shaped element that includes image sensor 350.

Figure 3D:
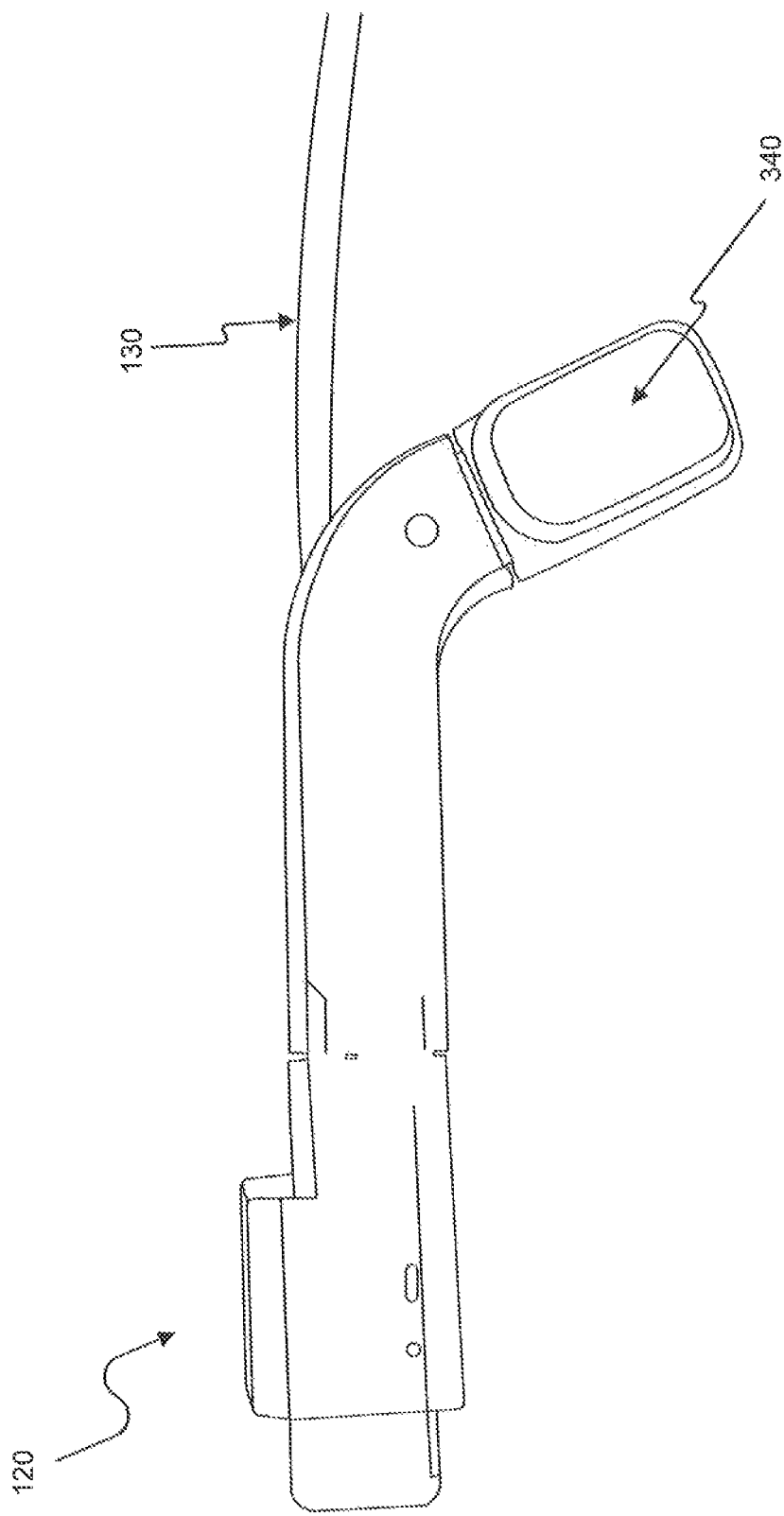
FIG. 3D is a schematic illustration of the sensory unit shown in FIG. 3A from a fourth viewpoint.

FIG. 3D is a schematic illustration of sensory unit 120 from a fourth viewpoint. The viewpoint shown in FIG. 3D is from an opposite side of the orientation shown in FIG. 3O. FIG. 3D shows the side of the U-shaped element that includes feedback-outputting unit 340.

Figure 3E:
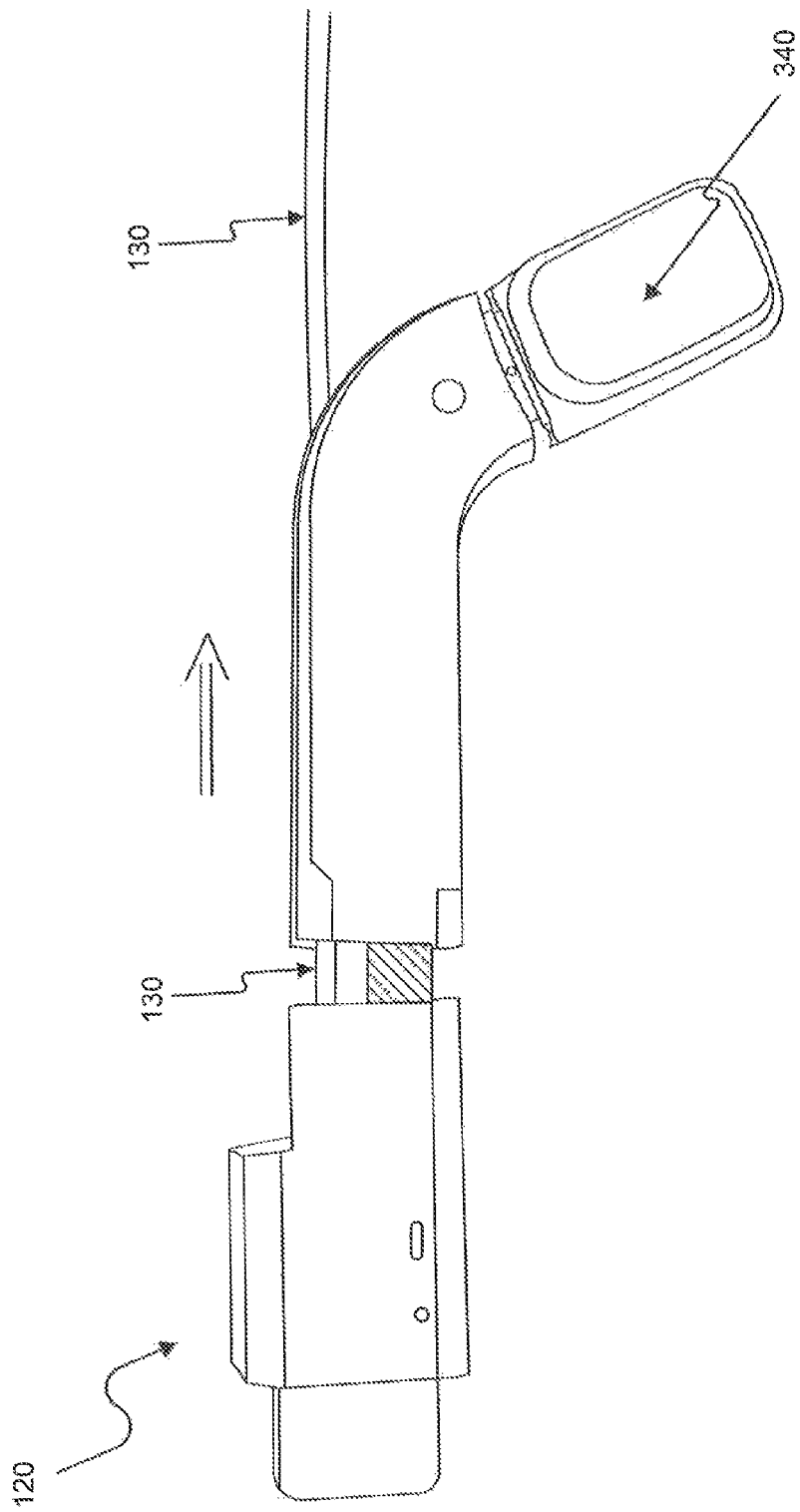
FIG. 3E is a schematic illustration of the sensory unit shown in FIG. 3A in an extended position.

FIG. 3E is a schematic illustration of the sensory unit shown in FIG. 3A in an extended position. As shown in FIG. 3E, a portion of sensory unit 120 is extendable and wire 130 may pass through a channel of sensory unit 120. This arrangement may allow a user to adjust the length and the angle of sensory unit 120 without interfering with the operation of apparatus 110.

User 100 may adjust the U-shaped element of sensory unit 120 so that feedback-outputting unit 340 is positioned adjacent to the user's ear or the user's temple. Accordingly, sensory unit 120 may be adjusted for use with different users who may have different head sizes. Alternatively, a portion of sensory unit 120 may be flexible such that the angle of feedback-outputting unit 340 is relative to the user's ear or the user's temple.

FIG. 4A is a schematic illustration of processing unit 140. As shown in FIG. 4A, processing unit 140 has a rectangular shape, which easily fits in a pocket of user 100. Processing unit 140 includes a connector 400 for connecting wire 130 to processing unit 140. Wire 130 may be used to transmit power from processing unit 140 to sensory unit 120, and data to and from processing unit 140 to sensory unit 120. Alternatively, wire 130 may comprise multiple wires (e.g., a wire dedicated to power transmission and a wire dedicated to data transmission).

Processing unit 140 includes a function button 410 for enabling user 100 to provide input to apparatus 110. Function button 410 may accept different types of tactile input (e.g., a tap, a click, a double-click, a long press, a right-to-left slide, a left-to-right slide). In some embodiments, each type of input may be associated with a different action. For example, a tap may be associated with the function of confirming an action, while a right-to-left slide may be associated with the function of repeating the last output.

FIG. 4B is a schematic illustration of processing unit 140 from a second viewpoint. As shown in FIG. 4B, processing unit 140 includes a volume switch 420, a battery pack compartment 430, and a power port 440. In one embodiment, user 100 may charge apparatus 110 using a charger connectable to power port 440. Alternatively, user 100 may replace a battery pack (not shown) stored in battery pack compartment 430.

Figure 5A:
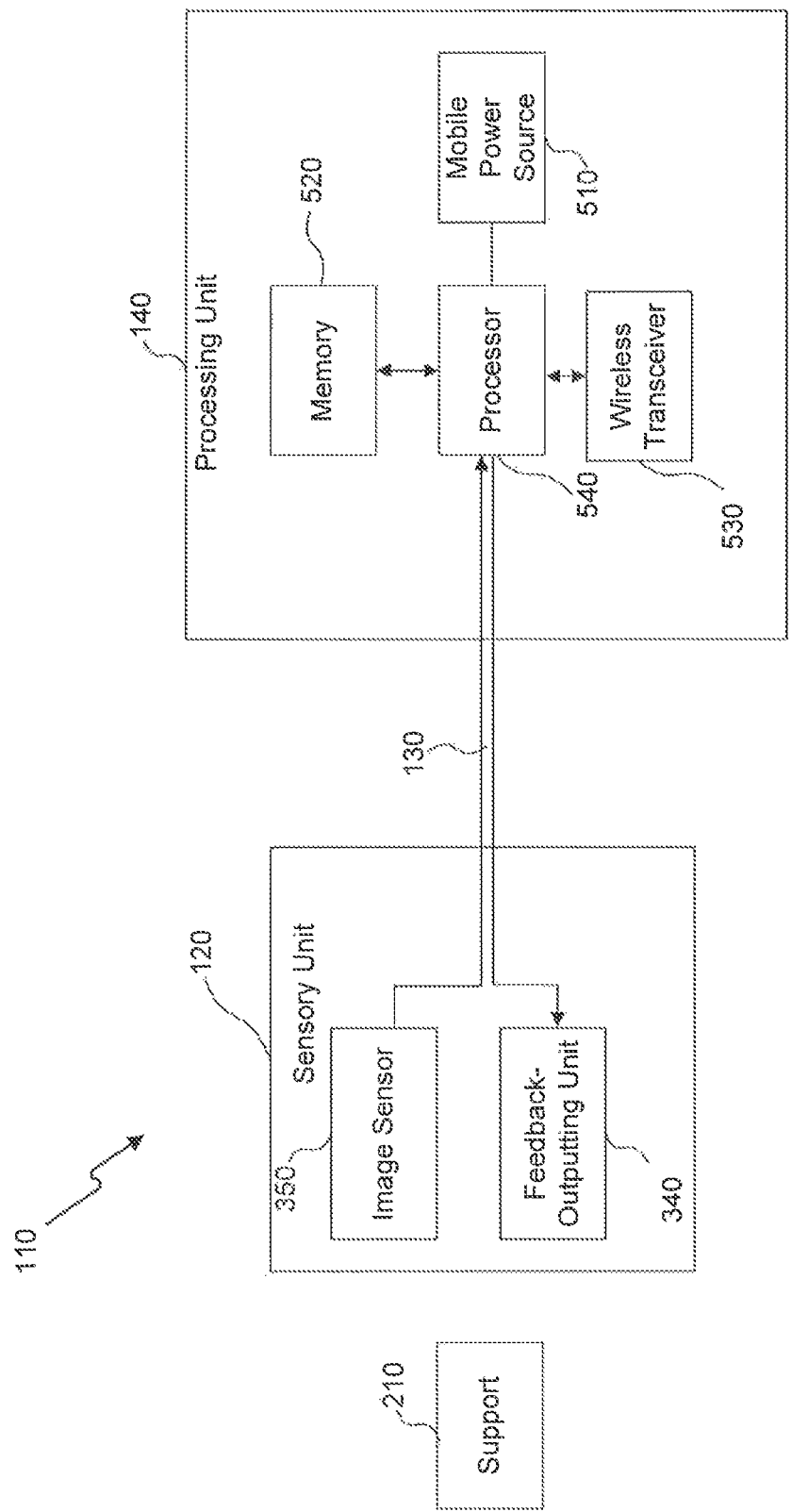
FIG. 5A is a block diagram illustrating an example of the components of an apparatus for aiding persons who have low vision according to a first embodiment.

FIG. 5A is a block diagram illustrating the components of apparatus 110 according to a first embodiment. Specifically, FIG. 5A depicts an embodiment in which apparatus 110 comprises sensory unit 120 and processing unit 140, as discussed in connection with, for example, FIG. 1. Furthermore, sensory unit 120 may be physically coupled to support 210.

As shown in FIG. 5A, sensory unit 120 includes feedback-outputting unit 340 and image sensor 350. Although one image sensor is depicted in FIG. 5A, sensory unit 120 may include a plurality of image sensors (e.g., two image sensors). For example, in an arrangement with more than one image sensor, each of the image sensors may be face a different direction or be associated with a different camera (e.g., a wide angle camera, a narrow angle camera, an IR camera, etc.). In other embodiments (not shown in the figure) sensory unit 120 may also include buttons and other sensors such as a microphone and inertial measurements devices.

As further shown in FIG. 5A, sensory unit 120 is connected to processing unit 140 via wire 130. Processing unit 140 includes a mobile power source 510, a memory 520, a wireless transceiver 530, and a processor 540.

Processor 540 may constitute any physical device having an electric circuit that performs a logic operation on input or inputs. For example, processor 540 may include one or more integrated circuits, microchips, microcontrollers, microprocessors, all or part of a central processing unit (CPU), graphics processing unit (GPU), digital signal processor (DSP), field-programmable gate array (FPGA), or other circuits suitable for executing instructions or performing logic operations. The instructions executed by processor 540 may, for example, be pre-loaded into a memory integrated with or embedded into processor 540 or may be stored in a separate memory (e.g., memory 520). Memory 520 may comprise a Random Access Memory (RAM), a Read-Only Memory (ROM), a hard disk, an optical disk, a magnetic medium, a flash memory, other permanent, fixed, or volatile memory, or any other mechanism capable of storing instructions.

Although one processor is shown in FIG. 5A, processing unit 140 may include more than one processor. Each processor may have a similar construction or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

In some embodiments, processor 540 may change the aiming direction of image sensor 350 using image data provided from image sensor 350. For example, processor 540 may recognize that a user is reading a book and determine that the aiming direction of image sensor 350 is offset from the text. That is, because the words in the beginning of each line of text are not fully in view, processor 540 may determine that image sensor 350 is tilted down and to the right. Responsive thereto, processor 540 may adjust the aiming direction of image sensor 350.

Processor 540 may access memory 520. Memory 520 may be configured to store information specific to user 100. For example, data for image representations of known individuals, favorite products, personal items, etc., may be stored in memory 520. In one embodiment, user 100 may have more than one pair of glasses, with each pair of glasses having support 210 mounted thereon. Accordingly, memory 520 may store information (e.g., personal settings) associated with each pair of glasses. For example, when a user wears his sunglasses may have different preferences than when the user wears reading glasses.

As shown in FIG. 5A, processing unit 140 includes mobile power source 510. Mobile power source 510 may be configured to power processing unit 140 and/or sensory unit 120. The term "mobile power source" includes any device capable of providing electrical power, which can be easily carried by a hand (e.g., the total weight of mobile power source 510 may be less than a pound). Thus, the mobility of the power source enables user 100 to use apparatus 110 in a variety of situations. For example, mobile power source 510 may include one or more batteries (e.g., nickel-cadmium batteries, nickel-metal hydride batteries, and lithium-ion batteries) or any other type of electrical power supply. In some embodiments, mobile power source 510 may be rechargeable and contained within a casing that holds processing unit 140. In other embodiments, mobile power source 510 may include one or more energy harvesting devices for converting ambient energy into electrical energy (e.g., portable solar power units, human vibration units, etc.).

Apparatus 110 may operate in a low-power-consumption mode and in a processing-power-consumption mode. For example, mobile power source 510 can produce five hours of processing-power-consumption mode and fifteen hours of low-power-consumption mode. Accordingly, different power consumption modes may allow mobile power source 510 to produce sufficient power for powering processing unit 140 for various time periods (e.g., more than two hours, more than four hours, more than ten hours, etc.).

Mobile power source 510 may power one or more wireless transceivers (e.g., wireless transceiver 530 in FIG. 5A). The term "wireless transceiver" refers to any device configured to exchange transmissions over an air interface by use of radio frequency, infrared frequency, magnetic field, or electric field. Wireless transceiver 530 may use any known standard to transmit and/or receive data (e.g., Wi-Fi, Bluetooth®, Bluetooth Smart, 802.15.4, or ZigBee). In some embodiments, wireless transceiver 530 may transmit data (e.g., raw image data or audio data) from image sensor 350 to processing unit 140, or wireless transceiver 530 may transmit data from processing unit 140 to feedback-outputting unit 340.

In another embodiment, wireless transceiver 530 may communicate with a different device (e.g., a hearing aid, the user's smartphone, or any wirelessly controlled device) in the environment of user 100. For example, wireless transceiver 530 may communicate with an elevator using a Bluetooth® controller. In such an arrangement, apparatus 110 may recognize that user 100 is approaching an elevator and call the elevator, thereby minimizing wait time. In another example, wireless transceiver 530 may communicate with a smart TV. In such an arrangement, apparatus 110 may recognize that user 100 is watching television and identify specific hand movements as commands for the smart TV (e.g., switching channels). In yet another example, wireless transceiver 530 may communicate with a virtual cane. A virtual cane is any device that uses a laser beam or ultrasound waves to determine the distance from user 100 to an object.

Figure 5B:
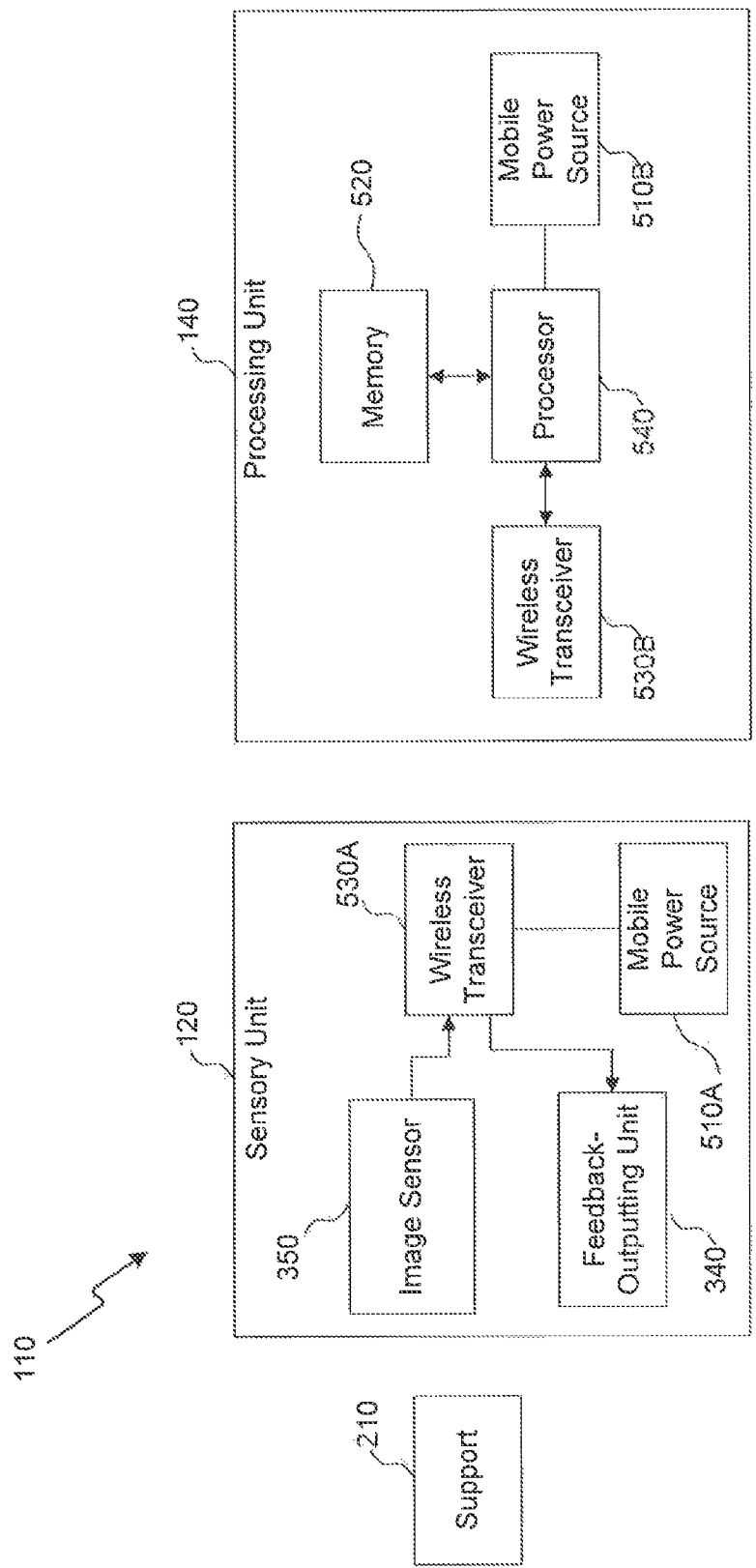
FIG. 5B is a block diagram illustrating an example of the components of an apparatus for aiding persons who have low vision according to a second embodiment.

FIG. 5B is a block diagram illustrating the components of apparatus 110 according to a second embodiment. In FIG. 5B, similar to the arrangement shown in FIG. 5A, support 210 is used to couple sensory unit 120 to a pair of glasses. However, in the embodiment shown in FIG. 5B, sensory unit 120 and processing unit 140 communicate wirelessly. For example, wireless transceiver 530A can transmit image data to processing unit 140 and receive information to be outputted via feedback-outputting unit 340.

In this embodiment, sensory unit 120 includes feedback-outputting unit 340, mobile power source 510A, wireless transceiver 530A, and image sensor 350. Mobile power source 510A is contained within sensory unit 120. As further shown in FIG. 5B, processing unit 140 includes wireless transceiver 530B, processor 540, mobile power source 510B, and memory 520.

Figure 5C:
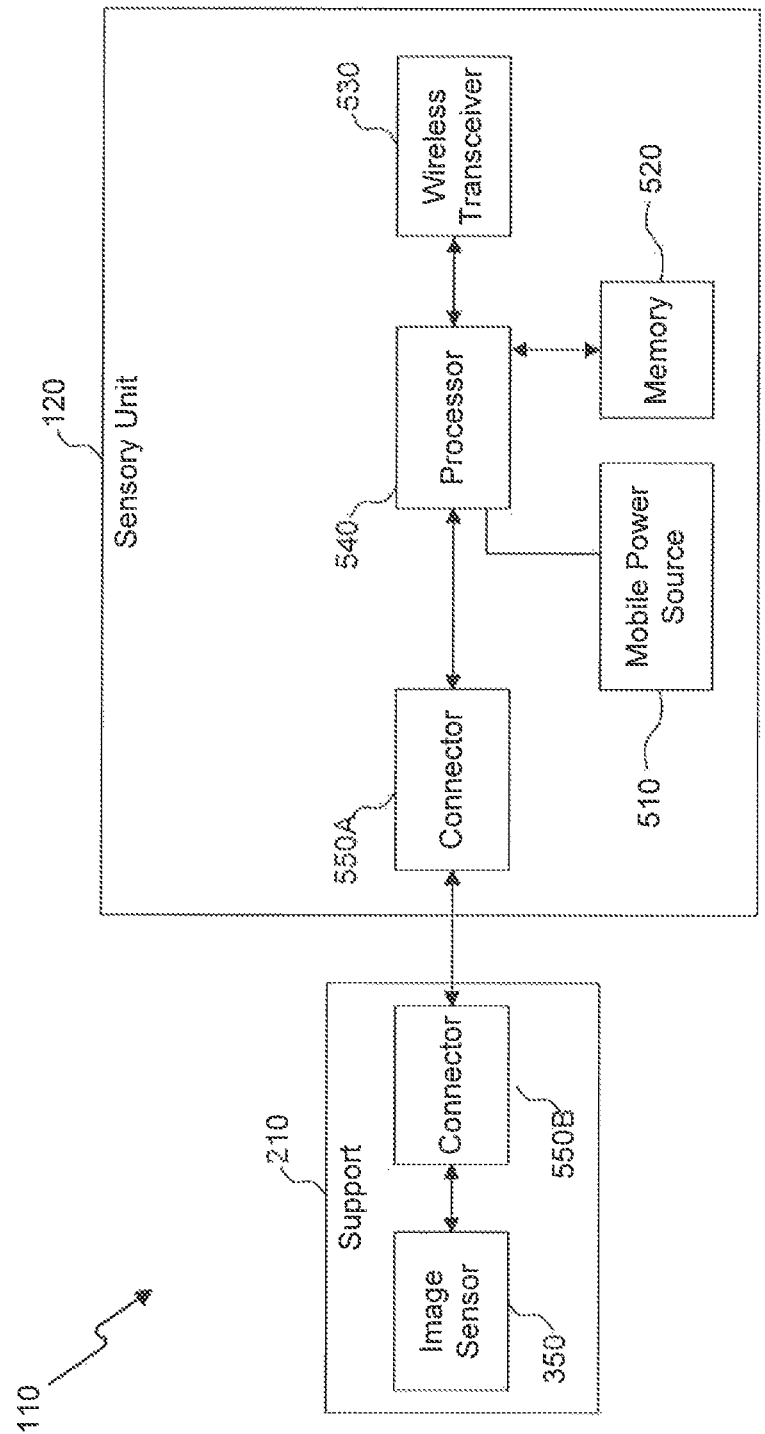
FIG. 5C is a block diagram illustrating an example of the components of an apparatus for aiding persons who have low vision according to a third embodiment.

FIG. 5C is a block diagram illustrating the components of apparatus 110 according to a third embodiment. In particular, FIG. 5C depicts an embodiment in which support 210 includes image sensor 350 and connector 550B. In this embodiment, sensory unit 120 provides functionality for processing data and, therefore, a separate processing unit is not needed in such a configuration.

As shown in FIG. 5C, sensory unit 120 includes processor 540, connector 550A, mobile power source 510, memory 520, and wireless transceiver 530. In this embodiment, apparatus 110 does not include a feedback-outputting unit. Accordingly, wireless transceiver 530 may communicate directly with a hearing aid (e.g., a Bluetooth® hearing aid). In addition, in this embodiment, image sensor 350 is included in support 210. Accordingly, when support 210 is initially mounted on glasses 105, image sensor 350 may acquire a set aiming direction. For example, a camera associated with image sensor 350 may be installed within support 210 in a predetermined angle in a position facing slightly downwards (e.g., 7-12 degrees from the horizon). Furthermore, connector 550A and connector 550B may allow data and power to be transmitted between support 210 and sensory unit 120.

Figure 5D:
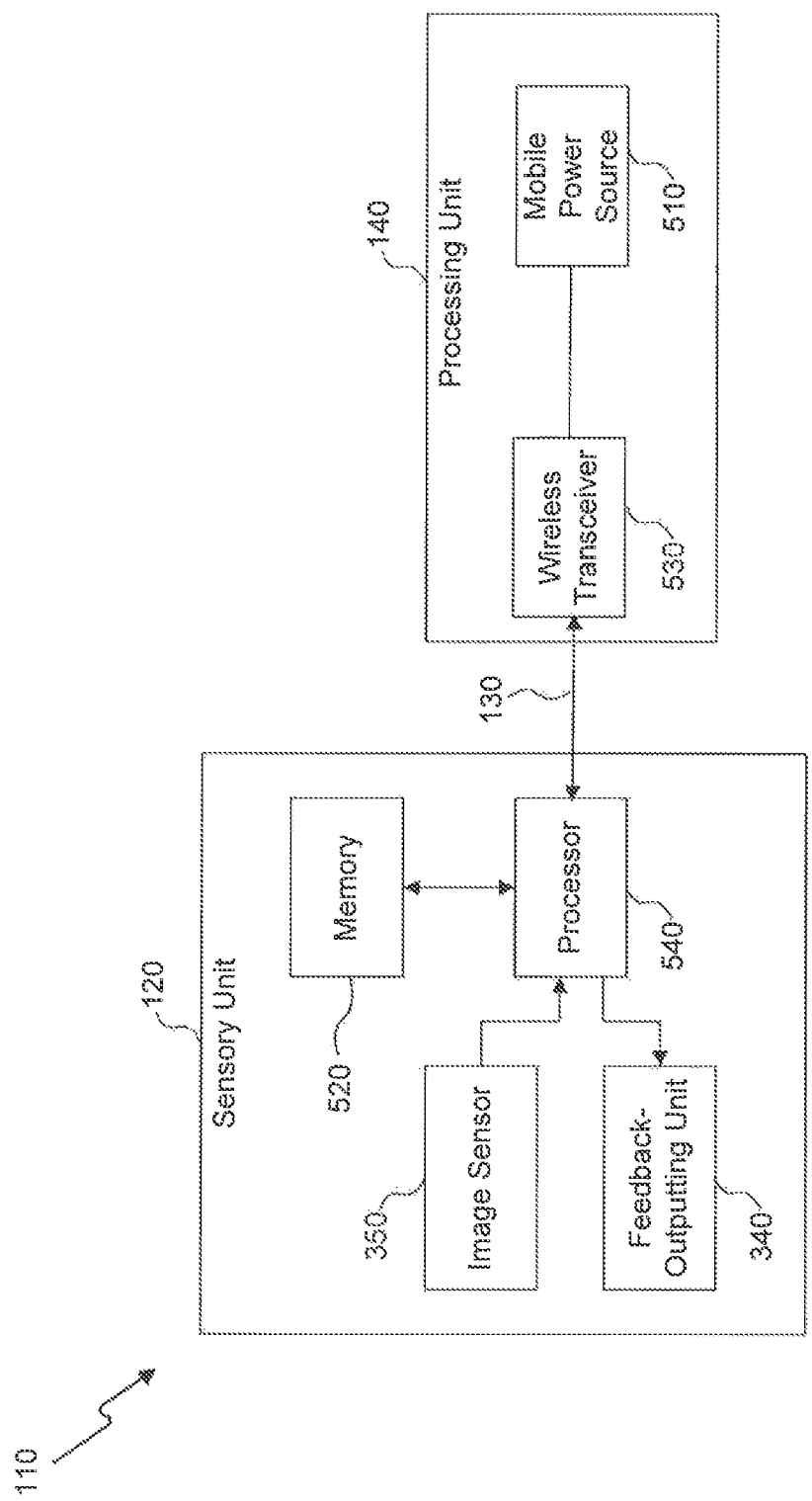
FIG. 5D is a block diagram illustrating an example of the components of an apparatus for aiding persons who have low vision according to a fourth embodiment.

FIG. 5D is a block diagram illustrating the components of apparatus 110 according to a fourth embodiment. In FIG. 5D, sensory unit 120 couples directly to a pair of glasses without the need of a support. In this embodiment, sensory unit 120 includes image sensor 350, feedback-outputting unit 340, processor 540, and memory 520. As shown in FIG. 5D, sensory unit 120 is connected via a wire 130 to processing unit 140. Additionally, in this embodiment, processing unit 140 includes mobile power source 510 and wireless transceiver 530.

As will be appreciated by a person skilled in the art having the benefit of this disclosure, numerous variations and/or modifications may be made to the disclosed embodiments. Not all components are essential for the operation of apparatus 110. Any component may be located in any appropriate part of apparatus 110 and the components may be rearranged into a variety of configurations while providing the functionality of the disclosed embodiments. Therefore, the foregoing configurations are examples and, regardless of the configurations discussed above, apparatus 110 can assist persons who have low vision with their everyday activities in numerous ways.

One way apparatus 110 can assist persons who have low vision is by identifying relevant objects in an environment. For example, in some embodiments, processor 540 may execute one or more computer algorithms and/or signal-processing techniques to find objects relevant to user 100 in image data captured by sensory unit 120. The term "object" refers to any physical object, person, text, or surroundings in an environment.

In one embodiment, apparatus 110 can perform a hierarchical object identification process. In a hierarchical object identification process, apparatus 110 can identify objects from different categories (e.g., spatial guidance, warning of risks, objects to be identified, text to be read, scene identification, and text in the wild) of image data. For example, apparatus 110 can perform a first search in the image data to identify objects from a first category, and after initiating the first search, execute a second search in the image data to identify objects from a second category.

In another embodiment, apparatus 110 can provide information associated with one or more of the objects identified in image data. For example, apparatus 110 can provide information such as the name of an individual standing in front of user 100. The information may be retrieved from a dynamic database stored in memory 520. If the database does not contain specific information associated with the object, apparatus 110 may provide user 100 with nonvisual feedback indicating that a search was made, but the requested information was not found in the database. Alternatively, apparatus 110 may use wireless transceiver 530 to search for and retrieve information associated with the object from a remote database (e.g., over a cellular network or Wi-Fi connection to the Internet).

Another way apparatus 110 can assist persons who have low vision is by performing a continuous action that relates to an object in an environment. A continuous action may involve providing continuous feedback regarding the object. For example, apparatus 110 can provide continuous feedback associated with an object identified within a field-of-view of image sensor 350, and suspend the continuous feedback when the object moves outside the field-of-view of image sensor 350. Examples of continuous feedback may include audibly reading text, playing a media file, etc. In addition, in some embodiments, apparatus 110 may provide continuous feedback to user 100 based on information derived from a discrete image or based on information derived from one or more images captured by sensory unit 120 from the environment of user 100.

Another type of continuous action includes monitoring the state of an object in an environment. For example, in one embodiment, apparatus 110 can track an object as long as the object remains substantially within the field-of-view of image sensor 350. Furthermore, before providing user 100 with feedback, apparatus 110 may determine whether the object is likely to change its state. If apparatus 110 determines that the object is unlikely to change its state, apparatus 110 may provide a first feedback to user 100. For example, if user 100 points to a road sign, apparatus 110 may provide a first feedback that comprises a descriptor of the road sign. However, if apparatus 110 determines that the object is likely to change its state, apparatus 110 may provide a second feedback to user 100 after the object has changed its state. For example, if user 100 points at a traffic light, the first feedback may comprise a descriptor of the current state of the traffic light (e.g., the traffic light is red) and the second feedback may comprise a descriptor indicating that the state of traffic light has changed (i.e., the traffic light is now green).

Apparatus 110 may also determine that an object that is expected to change its state is not functioning and provide appropriate feedback. For example, apparatus 110 may provide a descriptor indicating that a traffic light is broken.

Apparatus 110 can also assist persons who have low vision by making intelligent decisions regarding a person's intentions. Apparatus 110 can make these decisions by understanding the context of a situation. Accordingly, disclosed embodiments may retrieve contextual information from captured image data and adjust the operation of apparatus 110 based on at least the contextual information. The term "contextual information" (or "context") refers to any information having a direct or indirect relationship with an object in an environment. In some embodiments, apparatus 110 may retrieve different types of contextual information from captured image data. One type of contextual information is the time and/or the place that an image of the object was captured. Another example of a type of contextual information is the meaning of text written on the object. Other examples of types of contextual information include the identity of an object, the type of the object, the background of the object, the location of the object in the frame, the physical location of the user relative to the object, etc.

In an embodiment, the type of contextual information that is used to adjust the operation of apparatus 110 may vary based on objects identified in the image data and/or the particular user who wears apparatus 110. For example, when apparatus 110 identifies a package of cookies as an object, apparatus 110 may use the location of the package (i.e., at home or at the grocery store) to determine whether or not to read the list of ingredients aloud. Alternatively, when apparatus 110 identifies a signboard identifying arrival times for trains as an object, the location of the sign may not be relevant, but the time that the image was captured may affect the output. For example, if a train is arriving soon, apparatus 110 may read aloud the information regarding the coming train. Accordingly, apparatus 110 may provide different responses depending on contextual information.

Apparatus 110 may use contextual information to determine a processing action to execute or an image resolution of image sensor 350. For example, after identifying the existence of an object, contextual information may be used to determine if the identity of the object should be announced, if text written on the object should be audibly read, if the state of the object should be monitored, or if an image representation of the object should be saved. In some embodiments, apparatus 110 may monitor a plurality of images and obtain contextual information from specific portions of an environment. For example, motionless portions of an environment may provide background information that can be used to identify moving objects in the foreground.

Yet another way apparatus 110 can assist persons who have low vision is by automatically carrying out processing actions after identifying specific objects and/or hand gestures in the field-of-view of image sensor 350. For example, processor 540 may execute several actions after identifying one or more triggers in image data captured by apparatus 110. The term "trigger" includes any information in the image data that may cause apparatus 110 to execute an action. For example, apparatus 110 may detect as a trigger a finger of user 100 pointing to one or more coins. The detection of this gesture may cause apparatus 110 to calculate a sum of the value of the one or more coins. As another example of a trigger, an appearance of an individual wearing a specific uniform (e.g., a policeman, a fireman, a nurse) in the field-of-view of image sensor 350 may cause apparatus 110 to make an audible indication that this particular individual is nearby.

In some embodiments, the trigger identified in the image data may constitute a hand-related trigger. The term "hand-related trigger" refers to a gesture made by, for example, the user's hand, the user's finger, or any pointed object that user 100 can hold (e.g., a cane, a wand, a stick, a rod, etc.).

In other embodiments, the trigger identified in the image data may include an erratic movement of an object caused by user 100. For example, unusual movement of an object can trigger apparatus 110 to take a picture of the object. In addition, each type of trigger may be associated with a different action. For example, when user 100 points to text, apparatus 110 may audibly read the text. As another example, when user 100 erratically moves an object, apparatus 110 may audibly identify the object or store the representation of that object for later identification.

Apparatus 110 may use the same trigger to execute several actions. For example, when user 100 points to text, apparatus 110 may audibly read the text. As another example, when user 100 points to a traffic light, apparatus 110 may monitor the state of the traffic light. As yet another example, when user 100 points to a branded product, apparatus 110 may audibly identify the branded product. Furthermore, in embodiments in which the same trigger is used for executing several actions, apparatus 110 may determine which action to execute based on contextual information retrieved from the image data. In the examples above, wherein the same trigger (pointing to an object) is used, apparatus 110 may use the type of the object (text, a traffic light, a branded product) to determine which action to execute.

To assist user 100 throughout his or her daily activities, apparatus 100 may follow several procedures for saving processing resources and prolonging battery life. For example, apparatus 110 can use several image resolutions to form images. Higher image resolution provides more detailed images, but requires more processing resources. Lower image resolution provides less detailed images, but saves processing resources. Therefore, to prolong battery life, apparatus 110 may have rules for capturing and processing high resolution image under certain circumstances, and rules for capturing and processing low resolution image when possible. For example, apparatus 110 may capture higher resolution images when performing Optical Character Recognition (OCR), and capture low resolution images when searching for a trigger.

One of the common challenges persons with low vision face on a daily basis is reading. Apparatus 110 can assist persons who have low vision by audibly reading text that is present in user 100 environment. Apparatus 110 may capture an image that includes text using sensory unit 120. After capturing the image, to save resources and to process portions of the text that are relevant to user 100, apparatus 110 may initially perform a layout analysis on the text. The term "layout analysis" refers to any process of identifying regions in an image that includes text. For example, layout analysis may detect paragraphs, blocks, zones, logos, titles, captions, footnotes, etc.

In one embodiment, apparatus 110 can select which parts of the image to process, thereby saving processing resources and battery life. For example, apparatus 110 can perform a layout analysis on image data taken at a resolution of one megapixel to identify specific areas of interest within the text. Subsequently, apparatus 110 can instruct image sensor 350 to capture image data at a resolution of five megapixels to recognize the text in the identified areas. In other embodiments, the layout analysis may include initiating at least a partial OCR process on the text.

In another embodiment, apparatus 110 may detect a trigger that identifies a portion of text that is located a distance from a level break in the text. A level break in the text represents any discontinuity of the text (e.g., a beginning of a sentence, a beginning of a paragraph, a beginning of a page, etc.). Detecting this trigger may cause apparatus 110 to read the text aloud from the level break associated with the trigger. For example, user 100 can point to a specific paragraph in a newspaper and apparatus 110 may audibly read the text from the beginning of the paragraph instead of from the beginning of the page.

In addition, apparatus 110 may identify contextual information associated with text and cause the audible presentation of one portion of the text and exclude other portions of the text. For example, when pointing to a food product, apparatus 110 may audibly identify the calorie value of the food product. In other embodiments, contextual information may enable apparatus 110 to construct a specific feedback based on at least data stored in memory 520. For example, the specific feedback may assist user 100 to fill out a form (e.g., by providing user 100 audible instructions and details relevant to a form in the user's field-of-view).

To improve the audible reading capabilities of apparatus 110, processor 540 may use OCR techniques. The term "optical character recognition" includes any method executable by a processor to retrieve machine-editable text from images of text, pictures, graphics, etc. OCR techniques and other document recognition technology typically use a pattern matching process to compare the parts of an image to sample characters on a pixel-by-pixel basis. This process, however, does not work well when encountering new fonts, and when the image is not sharp. Accordingly, apparatus 110 may use an OCR technique that compares a plurality of sets of image regions that are proximate to each other. Apparatus 110 may recognize characters in the image based on statistics relate to the plurality of the sets of image regions. By using the statistics of the plurality of sets of image regions, apparatus 110 can recognize small font characters defined by more than four pixels e.g., six or more pixels. In addition, apparatus 110 may use several images from different perspectives to recognize text on a curved surface. In another embodiment, apparatus 110 can identify in image data an existence of printed information associated with a system command stored in a database and execute the system command thereafter. Examples of a system command include: "enter training mode," "enter airplane mode," "backup content," "update operating system," etc.

The disclosed OCR techniques may be implemented on various devices and systems and are not limited to use with apparatus 110. For example, the disclosed OCR techniques provide accelerated machine reading of text. In one embodiment, a system is provided for audibly presenting a first part of a text from an image, while recognizing a subsequent part of the text. Accordingly, the subsequent part may be presented immediately upon completion of the presentation of the first part, resulting in a continuous audible presentation of standard text in less than two seconds after initiating OCR.

As is evident from the foregoing, apparatus 110 may provide a wide range of functionality. More specifically, one embodiment consistent with the present disclosure provides a triggered action function. As has been described, apparatus 110 may be configured to perform one or more actions based on an identification of a trigger, such as a trigger present in captured image data, The triggered action function of apparatus 110 may allow a user (e.g., a visually-impaired user) to provide input to apparatus 110 (e.g., a trigger) in order to cause apparatus 110 to perform a pre-defined action. Examples of pre-defined actions include providing feedback (e.g., an audible descriptor) associated with an object, and storing a captured representation of an object, such as for providing feedback during future use of apparatus 110.

Figure 6:
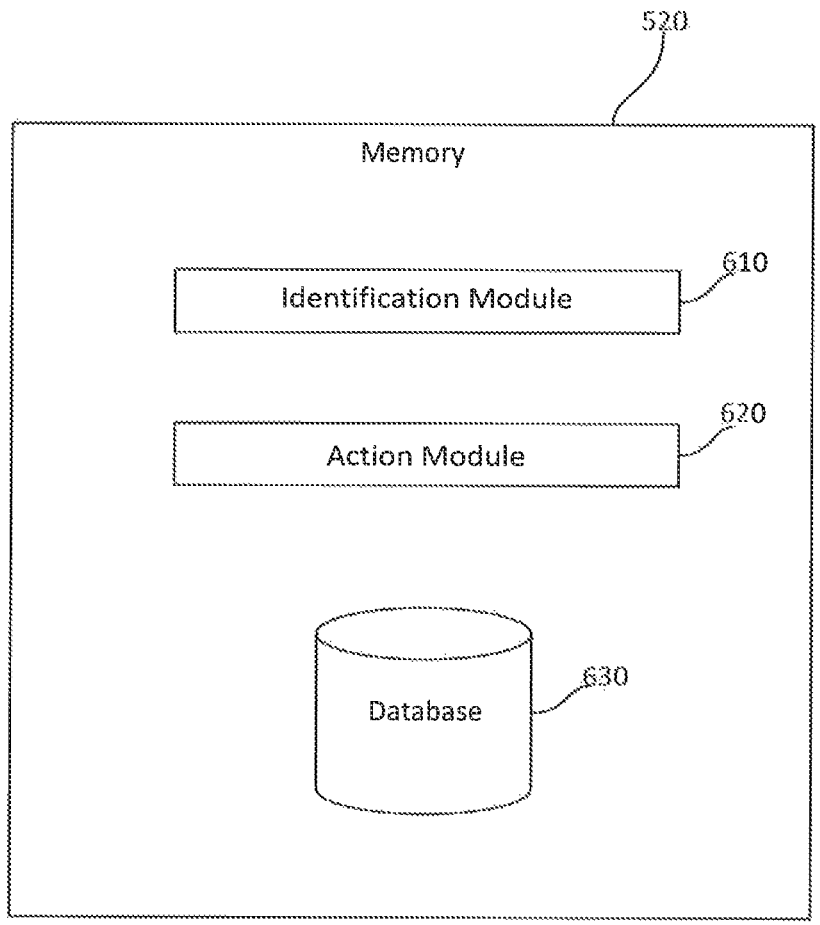
FIG. 6 is a block diagram illustrating an example of a memory configured to provide a triggered action function, consistent with disclosed embodiments.

In some embodiments, memory 520 may include components configured to provide the triggered action function. As shown in FIG. 6, memory 520 may include an identification module 610, an action module 620, and a database 630. Identification module 610 may be a component configured to identify a trigger based on image data captured by image sensor 350. Action module 620 may be a component configured to perform and/or cause apparatus 110 to perform a pre-defined action (e.g., in response to a trigger). Database 630 may be a component configured to store data associated with the triggered action function and provide particular data when requested.

Identification module 610 and action module 620 may be implemented in software, hardware, firmware, a mix of any of those, or the like. For example, if identification module 610 and action module 620 are implemented in software, they may be stored in memory 520, as shown in FIG. 6. Other components of processing unit 140 and/or sensory unit 120 may be configured to perform processes to implement and facilitate operations of identification module 610 and action module 620. Thus, identification module 610 and action module 620 may include software, hardware, or firmware instructions (or a combination thereof) executable by one or more processors (e.g., processor 540), alone or in various combinations with each other. For example, identification module 610 and action module 620 may be configured to interact with each other and/or other modules of apparatus 110 to perform functions consistent with disclosed embodiments. In some embodiments, any of the disclosed modules (e.g., identification module 610 and action module 620) may each include dedicated sensors (e.g., IR, image sensors, etc.) and/or dedicated application processing devices to perform the functionality associated with each module.

Database 630 may include one or more memory devices that store information and are accessed and/or managed through a computing device, such as processing unit 140. In some embodiments, database 630 may be located in memory 520, as shown in FIG. 6. In other embodiments, database 630 may be located remotely from memory 520, and be accessible to other components of apparatus 110 (e.g., processing unit 140) via one or more wireless connections (e.g., a wireless network). While one database 630 is shown, it should be understood that several separate and/or interconnected databases may make up database 630. Database 630 may include computing components (e.g., database management system, database server, etc.) configured to receive and process requests for data stored in memory devices associated with database 630 and to provide data from database 630.

In some embodiments, database 630 may be configured to store data associated with the triggered action function of apparatus 110. For example, database 630 may include recognized objects. In some embodiments, recognized objects may include captured representations of objects that were previously stored via apparatus 110. Recognized objects may be objects that apparatus 110 is configured to identify in real-time image data received by image sensor 350. Recognized objects may include any physical object, a person, an area, an environment, a background, and any combination and/or grouping of these. Recognized objects may include a particular aspect of an object (e.g., shape, color, text, etc.).

In some embodiments, database 630 may retain a plurality of representations and a plurality of descriptors, each descriptor associated with at least one stored representation. Each of the plurality of descriptors may include an audible representation, which may be provided to a user of apparatus 110, such as by feedback-outputting unit 340. In certain examples, at least one descriptor may be associated with at least two stored representations.

In some embodiments, database 630 may also be configured to store triggers, including triggers associated with the triggered action function of apparatus 110. Triggers may be any stored image or portion of an image that apparatus 110 may recognize as an input indicating a particular intention of the user of apparatus 110. For example, a pointing finger, a specific object, a particular hand motion, change in the field-of-view of apparatus 110, change in the user's area of focus, and the like, may be triggers. In some embodiments, triggers may include movements of objects. As has been described, an erratic movement of an object may be a trigger. In addition, other movements, such as a predefined movement sequence (e.g., a repetitive movement, a circular movement, a linear movement, etc.) may be stored as triggers. Apparatus 110 may be configured to identify movement of an object in image data to determine if the movement corresponds to a trigger.

After identifying a trigger in captured image data, apparatus 110 may perform a process to match the trigger to a trigger stored in database 630, although other trigger identification processes are possible. For example, apparatus 110 may be configured to estimate the trajectory of a moving object and analyze the trajectory for a corresponding trigger. Regardless of how apparatus 110 identifies a trigger, apparatus 110 may be further configured to identify a captured representation of an object associated with the trigger. Further, apparatus 110 may be configured to perform a pre-defined action based on the trigger and/or the captured representation.

Identification module 610 and action module 620 may be configured to communicate with each other and with database 630. For example, identification module 610 may monitor real-time image data to identify objects and triggers associated with the objects (e.g., movement of the object). If an object and a trigger are detected, identification module 610 may communicate with action module 620 to determine a pre-defined action associated with the object and/or the trigger. Action module 620 may communicate with components of apparatus 110 to cause apparatus 110 to perform the pre-defined action.

As used herein, real-time image data may refer to image data captured in real-time or near real-time. For example, identification module 610 may monitor the field-of-view of apparatus 110 to detect inputs while action module 620 may determine whether to initiate an action. Accordingly, identification module 610 and action module 620 may operate in parallel to process captured image data. That is, apparatus 110 may capture and analyze image data in parallel, or may institute a queue-like implementation whereby image data is captured and then analyzed in a continuous fashion (i.e., a first image is captured and analyzed while a subsequent image is captured and then subsequently analyzed).

Figure 7:
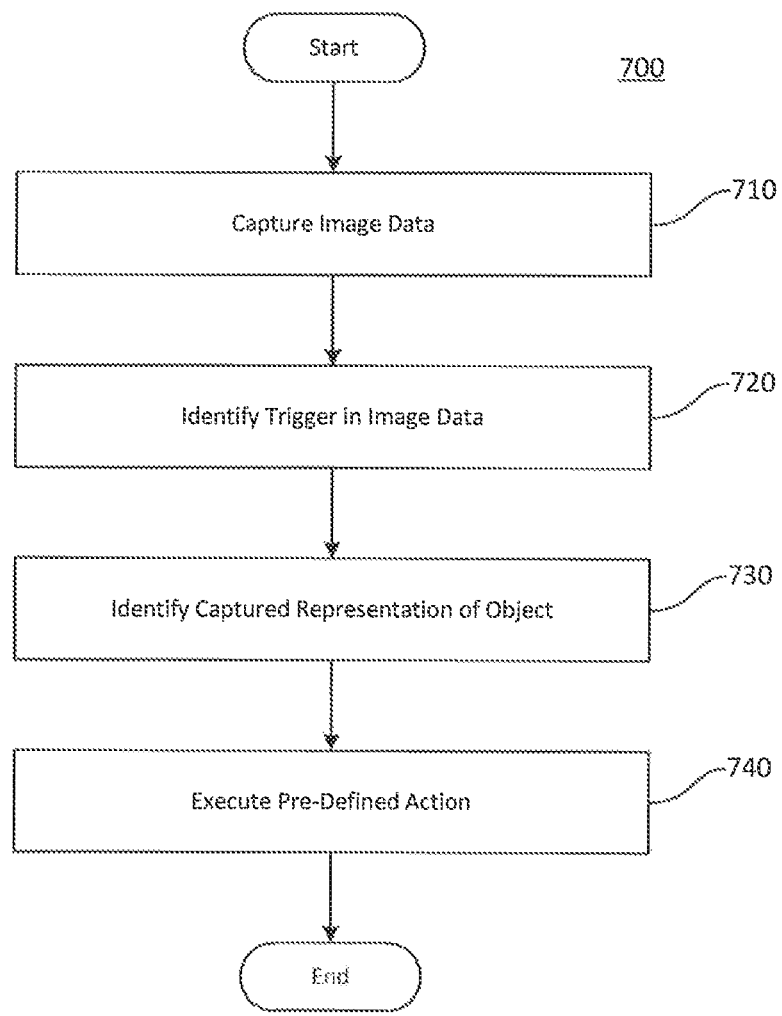
FIG. 7 is a flowchart of an example of a process for executing a pre-defined action in response to a trigger, consistent with disclosed embodiments.

FIG. 7 depicts a flowchart of an example process 700 for executing a pre-defined action in response to identification of a trigger. In some embodiments, identification module 610 and/or action module 620 may be configured to perform at least a part of process 700. Apparatus 110 may be arranged with image sensor 350 configured to capture image data from the environment of a user (e.g., a visually-impaired user of apparatus 110). In process 700, image sensor 350 may capture image data (step 710). In some embodiments, the image data may provide a plurality of sequential images of the user's environment. The images may include objects that are located within a field-of-view (e.g., a detectable area) of image sensor 350.

Identification module 610 may be configured to analyze the captured image data to look for objects and/or triggers. Consistent with process 700, identification module 610 may identify a trigger using the captured image data (step 720). In some aspects, the identified trigger may be associated with a desire of the user to cause at least one pre-defined action associated with an object (e.g., an object associated with the trigger). Identification module 610 may be configured to perform a trigger identification process to identify the trigger. An example of a trigger identification process will be described in more detail in the description of FIG. 8. In some embodiments, only a portion of the image data (e.g., a portion associated with a center area of a plurality of sequential images) may be used to identify the trigger.

In some embodiments, the trigger may be a movement of the object. For example, a user may hold an object in the field-of-view of image sensor 350 and move the object in a way (an "object movement") that corresponds to a trigger that matches a particular action associated with the object that the user is attempting to cause apparatus 110 to perform (e.g., identify the object, store a representation of the object, etc.).

One example of an object movement that corresponds to a trigger is an erratic movement of the object. For example, a user may move an object through an unusual or irregular path within the field-of-view of image sensor 350. Identification module 610 may be configured to identify the erratic movement of the object and determine that it matches a trigger. For example, identification module 610 may be configured to identify a particular number of changes in the movement of an object, with a sufficient number of changes indicating an erratic movement. A change in movement of an object may correspond to a change in direction, a change in speed, and/or a rotation, for example. In one embodiment, an erratic movement may include at least one detected change in the movement of an object. In another embodiment, an erratic movement may include at least two detected changes in the movement of an object.

Another example of an object movement that corresponds to a trigger is a predefined movement sequence of the object. For example, a user may move an object through a particular sequential path within the field-of-view of image sensor 350. Examples of particular sequential paths may include linear paths and circular paths. In another example, repetitive movement may be a predefined movement sequence of the object (e.g., waving of the object back and forth). Predefined movement sequences, as with erratic movements, may be defined by a particular number of changes in the movement of an object. For example, a predefined movement sequence may include at least two detected changes in the movement of the object. Examples of processes by which identification module 610 may identify a predefined movement sequence are described in more detail in the description of FIG. 8.

While identification module 610 has been described as configured to identify triggers in the image data, it should be understood that identification module 610 may additionally or alternatively be configured to identify a trigger without using the image data. For example, identification module 610 may identify input from function button 410 as a trigger. In certain embodiments, identification module 610 may be configured to identify a trigger without using the image data, in addition to a trigger, identified in the image data. In these embodiments, further processing to execute a pre-defined action may be initiated upon identification of both triggers.

In response to identification of the trigger, identification module 610 may identify in the image data a captured representation of the object (step 730). In some embodiments, the captured representation may include an image (or images) of the object. The image of the object may be cropped from an associated complete image, such that other objects, background information, etc., are removed from the image. In some embodiments, the captured representation of the object may be transmitted to action module 620 for further processing.

Action module 620 may receive notification of the trigger and/or the captured representation. Action module 620 may determine a pre-defined action associated with the trigger and/or the captured representation of the object. In addition, action module 620 may execute the pre-defined action (step 740). The pre-defined action may include providing feedback to the user, matching the captured representation to a stored representation, storing the captured representation, and/or the like. An example of a process for executing a pre-defined action will be described in more detail in the description of FIG. 14.

Figure 8:
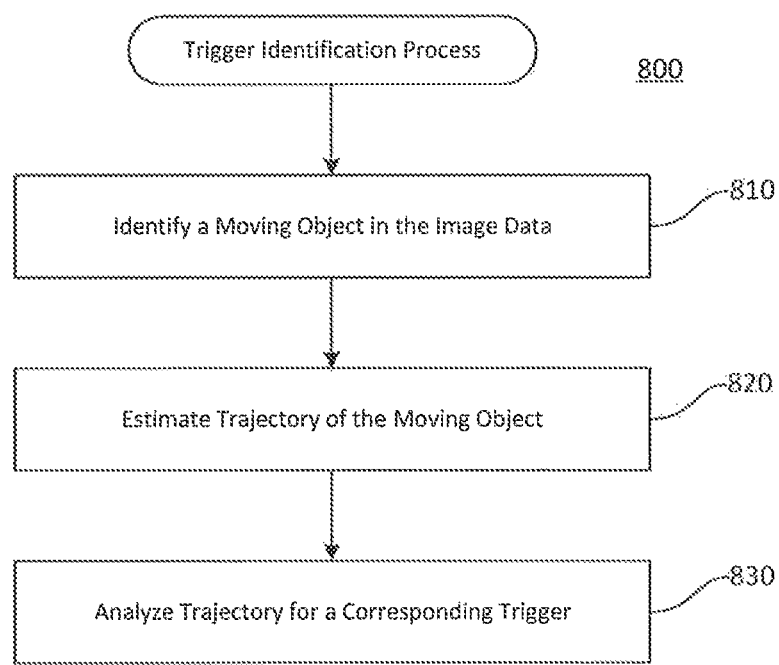
FIG. 8 is a flowchart of an example of a trigger identification process, which may be used conjunction with the process of FIG. 7.

FIG. 8 depicts a flowchart of an example trigger identification process 800. In some aspects, process 800 may correspond to step 720 of process 700. Identification module 610 may be configured to perform process 800 to identify a trigger in image data captured by image sensor 350. In some embodiments, identification module 610 may use trigger identification process 800 to isolate moving objects in a sequence of images captured by image sensor 350. In this way, identification module 610 may be configured to compare the movement of each isolated object with stored movements that are associated with a trigger.

In process 800, identification module 610 may first identify a moving object in the image data (step 810). In some embodiments, identification module 610 may be configured to identify a moving object by analyzing a sequence of images that include the object. For example, identification module 610 may be configured to recognize the same object at different locations within the sequential images, and therefore identify the object as a moving object. In some embodiments, identification module 610 may be configured to determine a shape of the object, which may be based on differences in the plurality of sequential images.

Once a moving object is identified, identification module 610 may be configured to estimate the trajectory of the moving object (step 820). In order to estimate the trajectory of the moving object, identification module 610 may use one or more algorithms to isolate the object within the sequence of images. For example, identification module 610 may use a segmentation algorithm to supply a bounding box around the moving object, such that the object (and the bounding box) may be tracked throughout the sequence of images. The bounding box may be generated based on key points in the image, which may correspond to points on a boundary of the object.

In some embodiments, identification of at least a portion of a user's hand may be used to isolate the object (and/or place a bounding box). The presence of the user's hand in the image may indicate that the user is holding the object (e.g., to move the object erratically), and therefore possibly represents a boundary of the object.

These and other techniques may be used to isolate the object in the image data. The isolated object may be tracked between the sequence of frames to produce an estimated movement trajectory.

In some embodiments, identification module 610 may analyze the estimated trajectory to determine if the estimated trajectory corresponds to a trigger (step 830). For example, identification module 610 may analyze an estimated trajectory of an object to determine if the movement of the object corresponds to an erratic movement trigger and/or a pre-defined movement sequence trigger. Identification module 610 may analyze an estimated trajectory for an erratic movement trigger by determining the number of changes in direction the object undergoes, for example. Similarly, identification module 610 may analyze an estimated trajectory for a predefined movement sequence by comparing the various locations of the object throughout the trajectory to the locations that may be expected for a particular predefined movement. If the estimated trajectory matches a particular trigger, the captured representation of the object (and/or the trigger) may be transmitted to action module 620 for further processing and execution of a pre-defined action.

Figure 9:
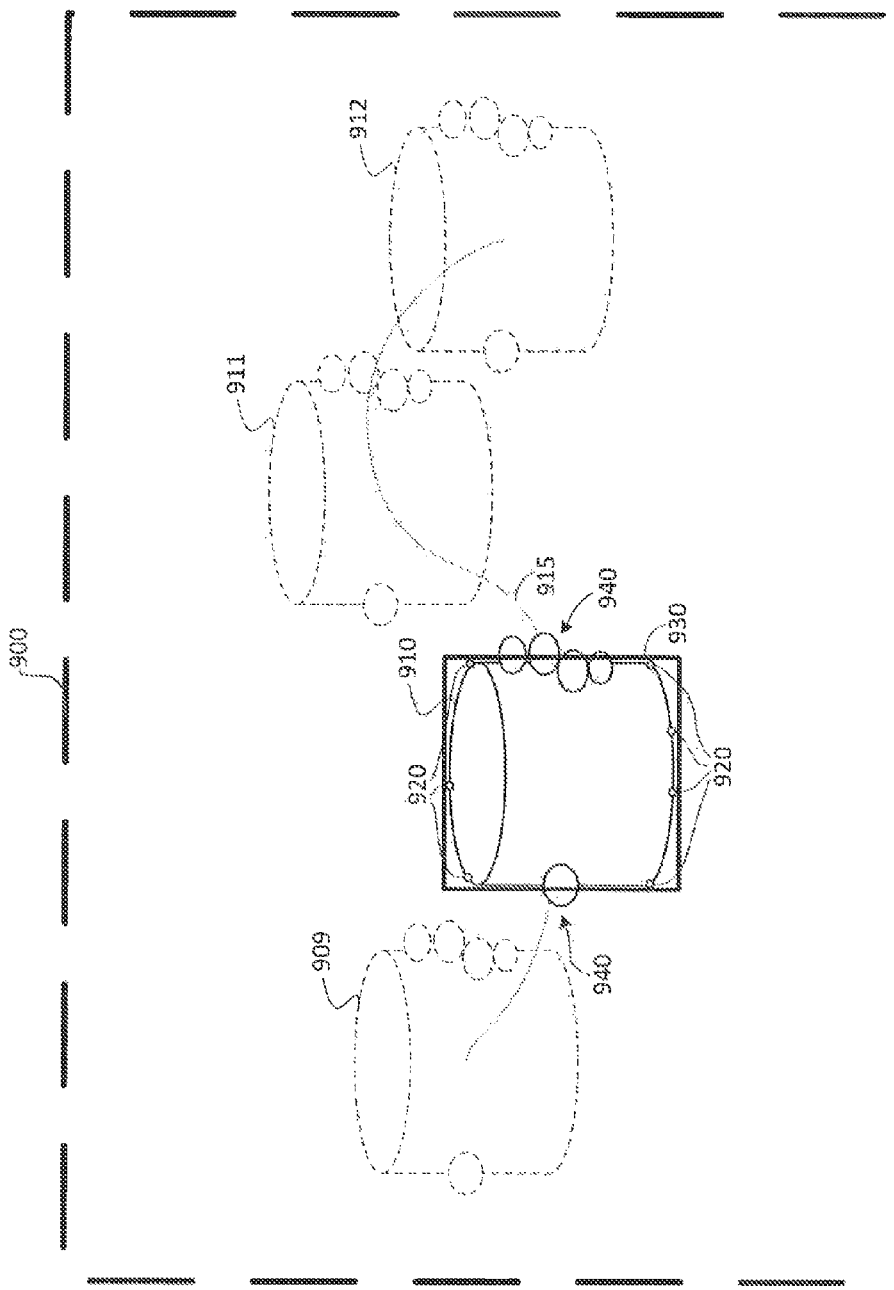
FIG. 9 is a schematic illustration of an image that includes an object, consistent with disclosed embodiments.

FIG. 9 depicts an example of an image 900 that may be captured by image sensor 350, the image including an object 910 that has been isolated by identification module 610. Identification module 610 may perform process 800 to analyze image 900, as well as any images that come before and/or after in a sequence of images captured by image sensor 350. For example, objects 909, 911, and 912 may indicate the location of object 910 in other images of the sequence, depicting object 910 as it travels on a path 915. Object 910 may represent any object of any shape or size observable by user 100.

Identification module 610 may use a segmentation algorithm to locate key points 920 in the image. Key points 920 may be points on or around the object that indicate a location of the object in the image. Key points 920 may be identified, for example, based on local image gradients in image 900, which may indicate a boundary of object 910. A bounding box 930 may be placed around the key points 920 in such a way that maximizes the density of the bounded key points 920. Bounding box 930 may be used as a constructive boundary of object 910, such that tracking of bounding box 930 through successive images may correspond to tracking of object 910.

In some embodiments, identification module 610 may be configured to look for a user's hand 940 in the image. The user's hand 940 may indicate that the object is being held by the user and may allow identification module 610 to localize object 910 within image 900. Additionally or alternatively, the portion of the user's hand 940 may be used to identify at least a portion of a boundary of object 910 (e.g., used as key points 920) and/or for placement of bounding box 930.

Based on the key points 920, bounding box 930, and/or portion of the user's hand 940, identification module 610 may track object 910 through a sequence of images to estimate the trajectory of the object (e.g., a path). As has been described, identification module 610 may determine whether the estimated trajectory corresponds to an object movement trigger, such as an erratic movement or a predefined movement sequence. Based on the trigger and a captured representation of the object, action module 620 may execute a pre-defined action, as described in the description of FIG. 7.

Figure 10:
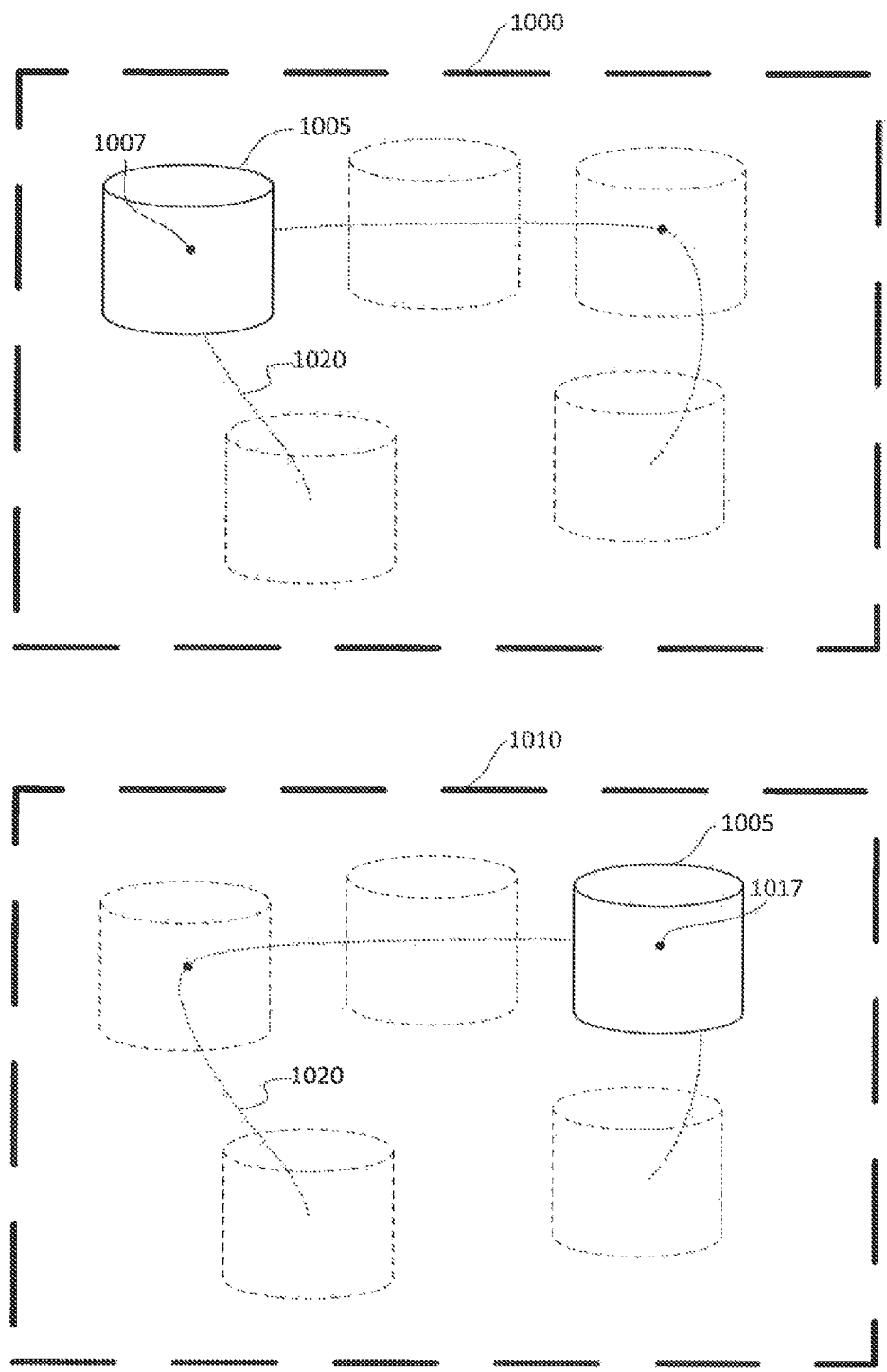
FIG. 10 is a schematic illustration of a sequence of images that depict an erratic movement of an object, consistent with disclosed embodiments.

FIG. 10 depicts an example of a sequence of images 1000 and 1010, each of which may be captured by image sensor 350 and which may include an object 1005. In one aspect, FIG. 10 may represent an example of an erratic movement trigger that identification module 610 may be configured to identify. As shown in FIG. 10, object 1005 may move through a path 1020. While images 1000 and 1010 are depicted in a sequence, it should be understood that one or more images may be captured between the time images 1000 and 1010 are captured. However, for ease of discussion, only these images are shown.

Image 1000 depicts object 1005 at a location 1007 within the field-of-view of image sensor 350. Identification module 610 may be configured to analyze image 1000 to isolate object 1005 at the location 1007. As shown by path 1050, location 1007 may indicate a first location along the path 1020 in which object 1005 changes movement (e.g., changes direction of movement). Identification module 610 may identify the first change in movement of object 1005 based on the location of object 1005 in images preceding and following image 1000. While not shown, in some embodiments, location 1007 may be an initial location of object 1005 and identification module 610 may be configured to identify a first change in movement based on a change in object 1005 from being stationary to being in-motion.

In some embodiments, identification module 610 may determine that the the first change in movement of object 1005 indicates an erratic movement trigger. In other embodiments, identification module 610 may continue to look for additional changes in movement of object 1005 before an erratic movement is identified.

Image 1010 depicts image 1005 at a second location 1017 within the field-of-view of image sensor 350. As shown by path 1050, location 1017 may indicate a second location along the path in which object 1005 changes movement (e.g., changes direction of movement). Based on the identification of the second change in movement, identification module 610 may determine that the movement of object 1005 corresponds to an erratic movement trigger. In other embodiments, identification module 610 may continue to look for changes in movement of object 1005 before an erratic movement is identified (e.g., 3 or more changes in movement). Based on the identified erratic movement trigger, action module 620 may execute a pre-defined action associated with object 1005.

Figure 11:
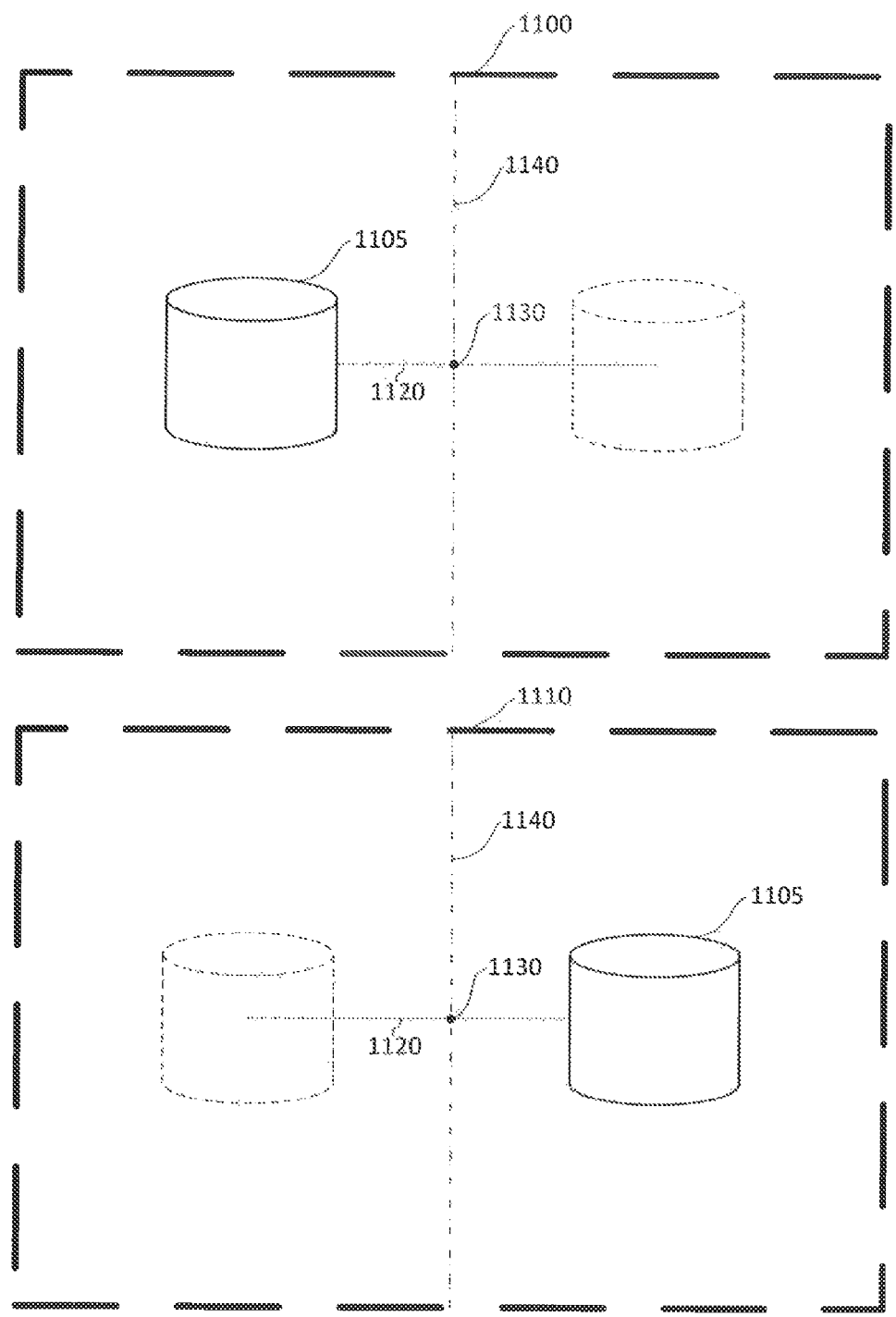
FIGS. 11-13 are schematic illustrations of sequences of images that depict various predefined movement sequences of an object, consistent with disclosed embodiments.

FIG. 11 depicts an example of a sequence of images 1100 and 1110, each of which may be captured by image sensor 350 and include an object 1105. In one aspect, FIG. 11 may represent an example of a predefined movement sequence trigger, corresponding to a repetitive movement of object 1105, that identification module 610 may be configured to identify. Images 1100 and 1110 may be selected images from a sequence of images that depict object 1105 moving along path 1120.

In some embodiments, identification module 610 may be configured to analyze the images of object 1105 moving along path 1120 to determine an average location 1130 of object 1105. Identification module 610 may further identify a line 1140 that passes through the average location 1130. In certain embodiments, identification module 610 may be configured to track the location of object 1105 throughout the sequence of images that include movement of object 1105 of path 1120 and compare the locations to the line 1140. Based on this comparison, identification module 610 may be configured to determine the number of times the object 1105 crosses the line 1140 while on the path 1120.

For example, image 1100 may depict object 1105 on one side of the line 1140 and image 1110 may depict object 1105 on the opposite side of the line 1140. As the object is repetitively moved, identification module 610 may identify the object 1105 as sequentially reaching the depicted positions on either side of line 1140, and determine that object 1105 is being moved in a predefined movement sequence that matches a trigger. In some embodiments, identification module 610 may be configured to look for particular criteria before identifying the movement as a trigger. For example, identification module 610 may determine the movement to be a repetitive movement associated with a trigger if it is determined that the object 1105 crosses the line 1140 a certain number of times (e.g., at least three times). Identification module 610 may also determine if object 1105 moves far enough away from the line 1140 between any two sequential crossings before considering the movement as a sufficient crossing.

Figure 12:
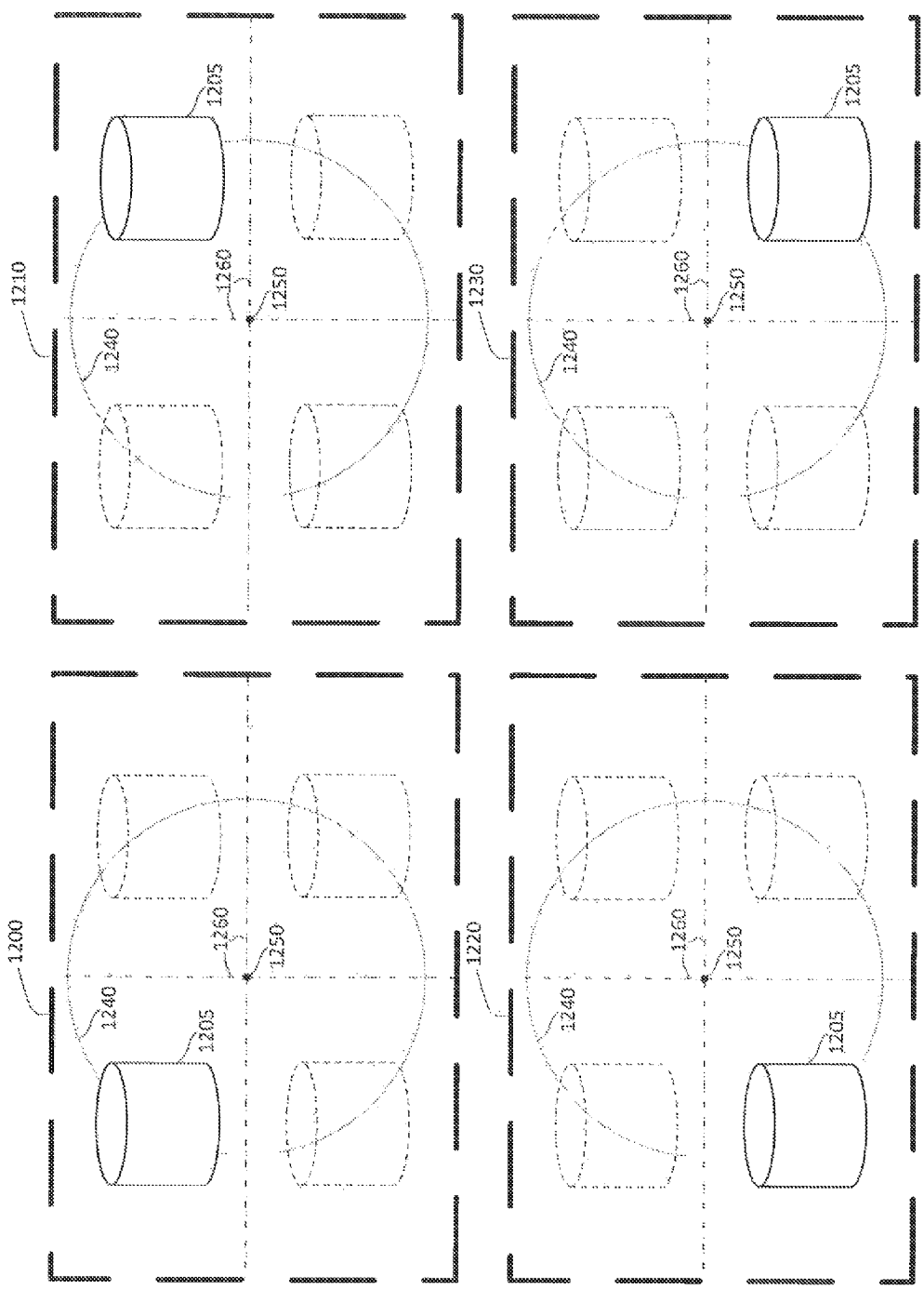

FIG. 12 depicts an example of a sequence of images 1200, 1210, 1220, and 1230, each of which may be captured by image sensor 350 and include object 1205. Similar to FIG. 11, FIG. 12 may represent another example of a predefined movement sequence that may be identified by identification module 610 as a trigger. In the example of FIG. 12, the predefined movement sequence may correspond to a circular movement of object 1205 along a path 1240. Images 1200, 1210, 1220, and 1230 may be images selected from a sequence of images that include object 1205 moving along path 1240.

Identification module 610 may analyze the images that include object 1205 moving along path 1240 to determine a center 1250 of the path 1240, which may be the center of a circle that correspond to path 1240. Identification module 610 may identify a pair of perpendicular lines 1260 that intersect at center 1250, the perpendicular lines dividing each image into four regions. Identification module 610 may track object 1205 throughout the images and compare the location of object 1205 in each image to the lines 1260. In some embodiments, identification module 610 may determine that the object 1205 has moved in a circular movement by determining that the object 1205 is sequentially located in each region during its movement along path 1240. Based on this determination, identification module 610 may be configured to identify the circular movement as a predefined movement sequence trigger. Images 1200, 1210, 1220, and 1230 depict examples of images that include object 1205 in one of each of the regions.

Figure 13:
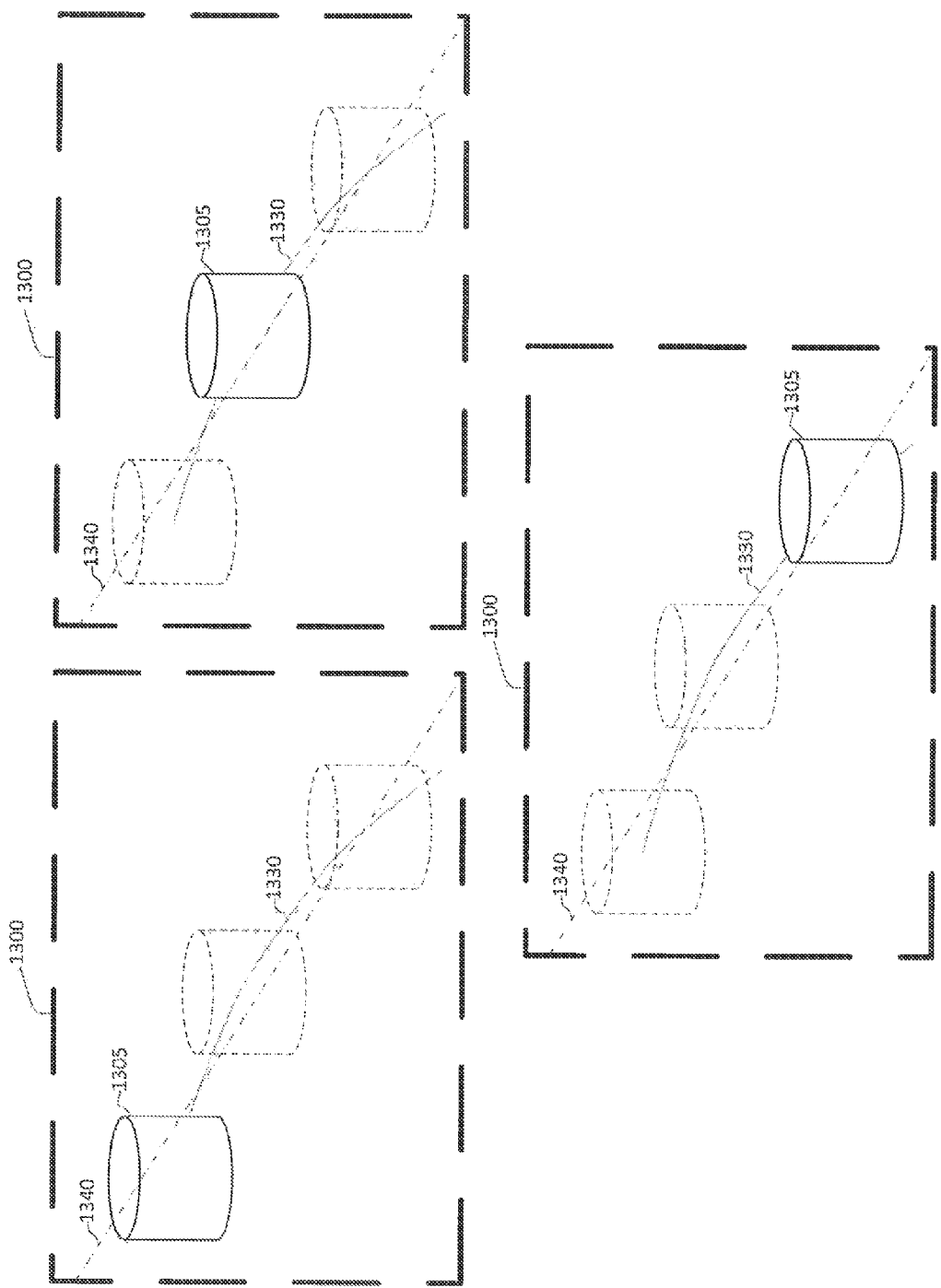

FIG. 13 depicts another example of a sequence of images 1300, 1310, and 1320, each of which may be captured by image sensor 350 and include an object 1305. Similar to FIGS. 11 and 12, FIG. 13 may represent yet another example of a predefined movement sequence that may be identified by identification module 610 as a trigger. In the example of FIG. 13, the predefined movement sequence may correspond to a linear movement of object 1305 along a path 1330. Images 1300, 1310, and 1320 may be images selected from a sequence of images that include object 1305 moving along path 1330.

In some embodiments, identification module 610 may be configured to analyze the images that include object 1305 moving along path 1330 to fit the points along the path 1330 (corresponding to the location of object 1305 in each of the images) to a two-dimensional line 1340, using a line equation (e.g., $a*x+b*y+c=0$). Identification module 610 may be further configured to determine a distance of each point to the line 1340, using a distance equation, for example. In some embodiments, identification module 610 may compare each distance to a threshold distance to determine if the points are sufficiently close to the line to constitute a predefined movement sequence. Based on this determination, identification module 610 may be configured to identify the linear movement as a predefined movement sequence trigger. Images 1300, 1310, and 1320 depict examples of images that include object 1305 at various locations along path 1330.

FIGS. 10-13 depict examples of object movements that identification module 610 may be configured to identify as triggers. It should be understood, however, that other processes for determining the object movements may be used. Similarly, other object movements may be used as triggers. As described in process 700, once a trigger is identified, identification module 610 may identify a captured representation of the object associated with the trigger. Based on the trigger and/or the captured representation of the object, action module 620 may determine and execute an associated pre-defined action.

Figure 14:
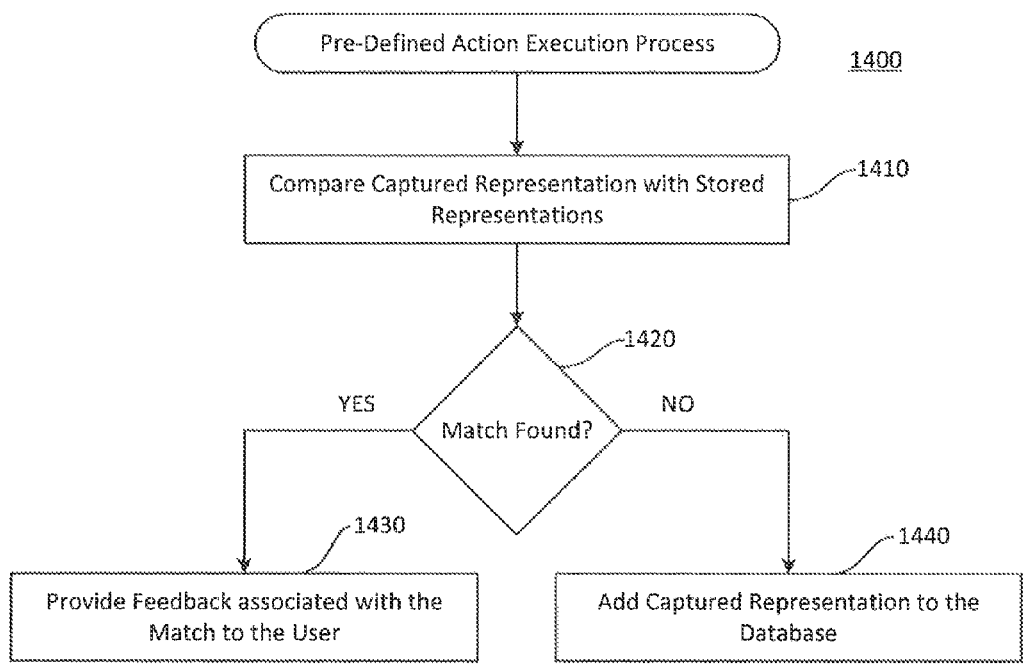
FIG. 14 is a flowchart of an example of a pre-defined action execution process, which may be used in conjunction with the process of FIG. 7.

FIG. 14 depicts a flowchart of an example of a pre-defined action execution process 1400. In some aspects, process 1400 may correspond to step 740 of process 700. That is, in some embodiments, action module 620 may be configured to perform process 1400 to execute a pre-defined action in response to identification of a trigger and a captured representation of an object associated with the trigger.

In certain embodiments, execution of the pre-defined action may include comparing the captured representation of the object with a plurality of stored representations (step 1410). For example, action module 620 may compare the captured representation with recognized objects stored in database 630. In some embodiments, a determined shape of the object may be used in comparing the captured representation with the plurality of stored representations. Execution of the pre-defined action may also include determining whether there is a match between the captured representation and the stored representations (step 1420).

If a match is identified (step 1420—YES), action module 620 may be configured to provide feedback to the user based on the match (step 1430). In some embodiments, the feedback may be an identification of the object, which may be based on a descriptor associated with the matched representation of the object. For example, in embodiments in which the plurality of stored representations are associated with a plurality of branded products, the feedback may include a descriptor of the branded product. The feedback may be provided to the user as audible feedback, for example, although other forms of feedback are possible.

If action module 620 determines that no match is found between the captured representation and the stored representations (step 1420—NO), action module 620 may be configured to add the captured representation of the object to a database (step 1440). For example, action module 620 may store the captured representation in database 630, along with additional information, such as a descriptor (e.g., an audible descriptor) of the object. In this way, future captured representations of the object may be matched to the stored representation to provide information (e.g., the audible descriptor) about the object. In some embodiments, action module 620 may additionally or alternatively be configured to provide audible feedback indicating that no match was found when no match is found.

In certain embodiments, action module 620 may be configured to additionally or alternatively perform other pre-defined actions. For example, in response to a trigger and a captured representation of an object, action module 620 may be configured to store in a memory the captured representation of the object and an audible descriptor of the object (e.g., with or without attempting to match the captured representation to stored representation), which may include associating the captured representation with an audible descriptor. In another example, action module 620 may be configured to execute a pre-defined action that includes detecting a barcode in the image data, decoding the barcode, and searching in a database (e.g., database 630) for a product associated with the decoded barcode.

The disclosed embodiments may allow apparatus 110 to provide a triggered action function. The triggered action function may allow a user to interact with apparatus 110 such that feedback associated with objects is provided to the user. Further, the use of various triggers in causing apparatus 110 to execute a variety of pre-defined actions may allow for efficient and customized use of apparatus 110.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks, floppy disks, or CD ROM, or other forms of RAM or ROM, USB media, DVD, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets. One or more of such software sections or modules can be integrated into a computer system or existing e-mail or browser software.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed routines may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. An apparatus for processing real time images of an environment of a user, the apparatus comprising:
a wearable image sensor configured to capture image data for providing a plurality of images of the environment of the user; and
at least one processor device configured to:
identify, using the image data, a trigger associated with a desire of the user to cause at least one pre-defined action associated with an object held in a hand of the user, wherein the trigger includes an erratic movement of the object and an identification of at least a portion of the hand holding the erratically moved object;
in response to identification of the trigger, identify in the image data a captured representation of the object; and
based on at least the captured representation of the object, execute the at least one pre-defined action.

2. The apparatus of claim 1, wherein the trigger includes at least one detected change in the movement of the object.

3. The apparatus of claim 1, wherein the trigger includes at least two detected changes in the movement of the object.

4. The apparatus of claim 1, wherein the at least one processor device is further configured to identify an additional trigger, without using the image data, and wherein execution of the at least one pre-defined action is initiated upon identifying the trigger and the additional trigger.

5. The apparatus of claim 1, wherein only a portion of the image data is used to identify the trigger.

6. The apparatus of claim 5, wherein the portion of the image data used to identify the trigger is associated with a center area of the plurality of images.

7. The apparatus of claim 1, wherein the at least one pre-defined action includes storing in a memory the captured representation of the object and an audible descriptor of the object.

8. The apparatus of claim 1, wherein the at least one pre-defined action includes comparing the captured representation of the object with a plurality of stored representations to identify a match and providing feedback to the user based on the match.

9. The apparatus of claim 8, wherein at least some of the plurality of stored representations are associated with a plurality of branded products and the feedback includes a descriptor of a branded product.

10. The apparatus of claim 1, wherein the at least one pre-defined action includes detecting a barcode in the image data, decoding the barcode, and searching in a database for a product associated with the decoded barcode.

11. An apparatus for processing real time images of an environment of a user, the apparatus comprising:
an image sensor configured to be worn by the user and to capture image data for providing a plurality of images of the environment of the user; and
at least one processor device configured to:
identify, using the image data, a trigger associated with a desire of the user to cause at least one pre-defined action associated with an object held in a hand of the user, wherein the trigger includes a predefined movement sequence of the object and an identification of at least a portion of the hand holding the erratically moved object;
in response to identification of the trigger, identify in the image data a captured representation of the object; and
based on at least the captured representation of the object, execute the at least one predefined action.

12. The apparatus of claim 11, wherein the predefined movement sequence includes at least two detected changes in the movement of the object.

13. The apparatus of claim 11, wherein the predefined movement sequence includes at least one of the following: a repetitive movement of the object, a circular movement of the object, and a linear movement of the object.

14. The apparatus of claim 11, wherein the at least one processor device is further configured to determine a shape of the object based on differences in the plurality of images.

15. The apparatus of claim 14, wherein the shape of the object is used in comparing the captured representation with a plurality of stored representations.

16. The apparatus of claim 11, wherein the apparatus further comprises at least one database for retaining a plurality of stored representations and a plurality of descriptors, wherein each descriptor is associated with at least one stored representation.

17. The apparatus of claim 16, wherein each of the plurality of descriptors includes an audible representation.

18. The apparatus of claim 16, wherein at least one descriptor is associated with at least two stored representations.

19. The apparatus of claim 11, wherein the at least one pre-defined action includes storing the captured representation and associating the captured representation with an audible descriptor.

20. The apparatus of claim 11, wherein the at least one pre-defined action includes comparing the captured representation of the object with a plurality of stored representations to identify a match and providing feedback to the user based on the match.

21. The apparatus of claim 20, wherein the at least one processor device is further configured to provide audible feedback indicating that no match was found when a match is not found.

22. The apparatus of claim 21, wherein the at least one processor device is further configured to add the captured representation of the object to a database when no match is found.

23. A method for providing feedback to a user, the method comprising:
capturing, via a wearable image sensor, real time image data from an environment of the user;
identifying in the image data a trigger associated with a desire of the user to cause at least one pre-defined action associated with an object held in a hand of the user, wherein the trigger includes an erratic movement of the object and an identification of at least a portion of the hand holding the erratically moved object; and
based on identification of the trigger:
identifying in the image data a captured representation of the object; and
based on at least the captured representation of the object, executing the at least one pre-defined action.

24. A software product stored on a non-transitory computer readable medium and comprising data and computer implementable instructions for carrying out the method of claim 23.

25. An apparatus for processing real time images of an environment of a user, the apparatus comprising:
   an image sensor configured to be worn by the user and to capture image data for providing a plurality of images of the environment of the user;
   at least one processor device configured to:
      identify, using the image data, a trigger associated with a desire of the user to cause at least one pre-defined action associated with an object, wherein the trigger includes a predefined movement sequence of the object;
      in response to identification of the trigger, identify in the image data a captured representation of the object; and
      based on at least the captured representation of the object, execute the at least one pre-defined action; and
   at least one database for retaining a plurality of stored representations and a plurality of descriptors, wherein each descriptor is associated with at least one stored representation, and each of the plurality of descriptors includes an audible representation.

26. The apparatus of claim 25, wherein at least one descriptor is associated with at least two stored representations.

27. An apparatus for processing real time images of an environment of a user, the apparatus comprising:
   a wearable image sensor configured to capture image data for providing a plurality of images of the environment of the user;
   at least one processor device configured to:
      identify, using the image data, a trigger associated with a desire of the user to cause at least one pre-defined action associated with an object held in a hand of the user, wherein the trigger includes an erratic movement of the object;
      in response to identification of the trigger, identify in the image data a captured representation of the object; and
      based on at least the captured representation of the object, execute the at least one pre-defined action; and
   at least one database for retaining a plurality of stored representations and a plurality of descriptors, wherein each descriptor is associated with at least one stored representation, and each of the plurality of descriptors includes an audible representation.

28. The apparatus of claim 27, wherein at least one descriptor is associated with at least two stored representations.

* * * * *